(12) United States Patent
Hansson et al.

(10) Patent No.: US 9,895,109 B2
(45) Date of Patent: Feb. 20, 2018

(54) MONITORING OF CARDIAC ARREST IN A PATIENT CONNECTED TO AN EXTRACORPOREAL BLOOD PROCESSING APPARATUS

(71) Applicants: GAMBRO LUNDIA AB, Lund (SE); Anders Onshage, Lund (SE)

(72) Inventors: Per Hansson, Akarp (SE); Bo Olde, Lund (SE); Kristian Solem, Kavlinge (SE); Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 158 days.

(21) Appl. No.: 14/777,695

(22) PCT Filed: Mar. 17, 2014

(86) PCT No.: PCT/EP2014/055309
§ 371 (c)(1),
(2) Date: Sep. 16, 2015

(87) PCT Pub. No.: WO2014/147028
PCT Pub. Date: Sep. 25, 2014

(65) Prior Publication Data
US 2016/0270733 A1 Sep. 22, 2016

(30) Foreign Application Priority Data
Mar. 20, 2013 (SE) ...................................... 1350344

(51) Int. Cl.
*A61B 5/02* (2006.01)
*A61B 5/00* (2006.01)
(Continued)

(52) U.S. Cl.
CPC .......... *A61B 5/6866* (2013.01); *A61B 5/0215* (2013.01); *A61B 5/02125* (2013.01);
(Continued)

(58) Field of Classification Search
None
See application file for complete search history.

(56) References Cited

U.S. PATENT DOCUMENTS 3,882,861 A  5/1975 Kettering et al.
3,946,731 A  3/1976 Lichtenstein
(Continued)

FOREIGN PATENT DOCUMENTS

DE  196 09 698  9/1997
DE  198 48 235  3/2000
(Continued)

OTHER PUBLICATIONS

Sasson et al., "Predictors of Survival From Out-of-Hospital Cardiac Arrest: A Systematic Review and Meta-Analysis," Circulation Cardiovascular Quality and Outcomes, American Heart Association, Jan. 2010, 3; pp. 63-81
(Continued)

*Primary Examiner* — Ankit D Tejani
(74) *Attorney, Agent, or Firm* — K&L Gates LLP

(57) ABSTRACT

A monitoring device (7) operates an input block (30) to acquire a pressure signal from a pressure sensor (6a-6c) in an apparatus for extracorporeal blood processing connected to the vascular system of the subject. A processing block (34) repeatedly processes the pressure signal for generation of a time-sequence of parameter values indicative of pressure pulsations originating from heartbeats in the subject, and an evaluation block (35) evaluates the parameter values for detection of cardiac arrest and, if cardiac arrest is detected, generates a dedicated alarm signal. To reduce the risk for false positives without increasing the risk for false negatives, the monitoring device (7) may acquire and process more than one pressure signal, and/or perform an initial viability check before the monitoring is initiated to ensure that pressure pulsations originating from heartbeats are
(Continued)

detectable in the pressure signal(s), and/or separate the monitoring of the pressure signal(s) into a detection phase performed during regular operation of a blood pump in the apparatus, and a verification phase performed during a temporary shutdown of the blood pump.

49 Claims, 11 Drawing Sheets

(51) Int. Cl.
    *A61B 5/0215*     (2006.01)
    *A61M 1/36*     (2006.01)
    *A61B 5/021*     (2006.01)

(52) U.S. Cl.
    CPC ........ *A61B 5/02158* (2013.01); *A61B 5/4836* (2013.01); *A61B 5/7246* (2013.01); *A61B 5/7282* (2013.01); *A61B 5/746* (2013.01); *A61M 1/369* (2013.01); *A61M 1/3639* (2013.01); *A61M 1/3653* (2013.01); *A61M 2230/04* (2013.01)

(56) References Cited

U.S. PATENT DOCUMENTS

| | | |
|---|---|---|
| 4,185,641 A | 1/1980 | Minior et al. |
| 4,239,047 A | 12/1980 | Griggs, III et al. |
| 4,277,227 A | 7/1981 | Jenkins |
| 4,353,368 A | 10/1982 | Slovak et al. |
| 4,392,847 A | 7/1983 | Whitney et al. |
| 4,450,527 A | 5/1984 | Sramek |
| 4,501,483 A | 2/1985 | Romansky et al. |
| 4,534,756 A | 8/1985 | Nelson |
| 4,541,282 A | 9/1985 | Auerweck et al. |
| 4,648,869 A | 3/1987 | Bobo, Jr. |
| 4,710,163 A | 12/1987 | Butterfield |
| 4,828,543 A | 5/1989 | Weiss et al. |
| 4,846,792 A | 7/1989 | Bobo, Jr. et al. |
| 4,923,598 A | 5/1990 | Schal |
| 4,959,050 A | 9/1990 | Bobo, Jr. |
| 4,972,826 A | 11/1990 | Koehler et al. |
| 4,979,940 A | 12/1990 | Bobo, Jr. et al. |
| 4,981,467 A | 1/1991 | Bobo, Jr. et al. |
| 5,026,348 A | 6/1991 | Venegas |
| 5,100,374 A | 3/1992 | Kageyama |
| 5,146,414 A | 9/1992 | McKown et al. |
| 5,311,871 A | 5/1994 | Yock |
| 5,427,695 A | 6/1995 | Brown |
| 5,557,263 A | 9/1996 | Fisher et al. |
| 5,693,008 A | 12/1997 | Brugger et al. |
| 5,790,036 A | 8/1998 | Fisher et al. |
| 5,830,365 A | 11/1998 | Schneditz |
| 5,863,421 A | 1/1999 | Peter, Jr. et al. |
| 5,910,252 A | 6/1999 | Truitt et al. |
| 6,066,261 A | 5/2000 | Spickermann |
| 6,071,421 A | 6/2000 | Brown |
| 6,077,443 A | 6/2000 | Goldau |
| 6,090,048 A | 7/2000 | Hertz et al. |
| 6,167,765 B1 | 1/2001 | Weitzel |
| 6,187,199 B1 | 2/2001 | Goldau |
| 6,200,485 B1 | 3/2001 | Kitaevich et al. |
| 6,221,040 B1 | 4/2001 | Kleinekofort |
| 6,337,049 B1 | 1/2002 | Tamari |
| 6,572,576 B2 | 6/2003 | Brugger et al. |
| 6,575,927 B1 | 6/2003 | Weitzel et al. |
| 6,595,942 B2 | 7/2003 | Kleinekofort |
| 6,623,443 B1 | 9/2003 | Polaschegg |
| 6,649,063 B2 | 11/2003 | Brugger et al. |
| 6,663,585 B1 | 12/2003 | Ender |
| 6,730,055 B2 | 5/2004 | Bainbridge et al. |
| 6,736,789 B1 | 5/2004 | Spickermann |
| 6,767,333 B1 | 6/2004 | Muller et al. |
| 6,773,670 B2 | 8/2004 | Stringer et al. |
| 6,780,159 B2 | 8/2004 | Sandler et al. |
| 6,804,991 B2 | 10/2004 | Balschat et al. |
| 6,827,698 B1 | 12/2004 | Kleinekofort |
| 6,880,404 B2 | 4/2005 | Uberreiter |
| 6,899,691 B2 | 5/2005 | Bainbridge et al. |
| 6,979,306 B2 | 12/2005 | Moll |
| 7,040,142 B2 | 5/2006 | Burbank |
| 7,060,047 B2 | 6/2006 | Lodi et al. |
| 7,087,033 B2 | 8/2006 | Brugger et al. |
| 7,169,352 B1 | 1/2007 | Felt et al. |
| 7,172,569 B2 | 2/2007 | Kleinekofort |
| 7,172,570 B2 | 2/2007 | Cavalcanti et al. |
| 7,276,041 B2 | 10/2007 | Moll |
| 7,410,473 B2 | 8/2008 | Levin et al. |
| 7,537,687 B2 | 5/2009 | Toyoda et al. |
| 7,615,028 B2 | 11/2009 | O'Mahony |
| 8,152,751 B2 | 4/2012 | Roger et al. |
| 8,197,421 B2 | 6/2012 | Freeman et al. |
| 8,603,020 B2 | 12/2013 | Roger et al. |
| 2001/0007930 A1 | 7/2001 | Kleinekofort |
| 2002/0004636 A1 | 1/2002 | Tsubata |
| 2002/0198483 A1 | 12/2002 | Wariar et al. |
| 2003/0009123 A1 | 1/2003 | Brugger et al. |
| 2003/0128125 A1 | 7/2003 | Burbank et al. |
| 2003/0130607 A1 | 7/2003 | Delvano et al. |
| 2003/0152482 A1 | 8/2003 | O'Mahony et al. |
| 2004/0030277 A1 | 2/2004 | O'Mahony et al. |
| 2004/0041792 A1 | 3/2004 | Criscione |
| 2004/0171977 A1 | 9/2004 | Paolini et al. |
| 2004/0186409 A1 | 9/2004 | Cavalcanti et al. |
| 2004/0228760 A1 | 11/2004 | Stringer et al. |
| 2005/0004502 A1 | 1/2005 | O'Mahony et al. |
| 2005/0004636 A1* | 1/2005 | Noda .............. A61F 7/12 607/105 |
| 2005/0010118 A1 | 1/2005 | Toyoda et al. |
| 2005/0131332 A1 | 6/2005 | Kelly et al. |
| 2005/0230313 A1 | 10/2005 | O'Mahony et al. |
| 2006/0081517 A1 | 4/2006 | Toyoda et al. |
| 2006/0122552 A1 | 6/2006 | O'Mahony |
| 2007/0004996 A1 | 1/2007 | Lovejoy et al. |
| 2007/0004997 A1 | 1/2007 | Felt et al. |
| 2007/0010779 A1 | 1/2007 | Utterberg et al. |
| 2007/0078368 A1 | 4/2007 | Felt et al. |
| 2007/0093774 A1 | 4/2007 | Felt et al. |
| 2007/0108128 A1 | 5/2007 | Koperschmidt et al. |
| 2007/0112289 A1 | 5/2007 | Cavalcanti et al. |
| 2007/0179433 A1 | 8/2007 | Jonsson et al. |
| 2007/0232980 A1 | 10/2007 | Felt et al. |
| 2008/0183120 A1 | 1/2008 | Utterberg et al. |
| 2008/0108930 A1 | 5/2008 | Weitzel et al. |
| 2008/0171960 A1 | 7/2008 | Brieske et al. |
| 2008/0195022 A1 | 8/2008 | Lucke et al. |
| 2008/0214979 A1 | 9/2008 | Brugger et al. |
| 2009/0078622 A1 | 3/2009 | Zhang et al. |
| 2010/0234786 A1 | 9/2010 | Fulkerson et al. |
| 2011/0105982 A1* | 5/2011 | Leonard .............. A61M 1/14 604/6.01 |
| 2011/0106466 A1 | 5/2011 | Furmanski et al. |
| 2011/0112442 A1 | 5/2011 | Meger et al. |
| 2011/0230772 A1 | 9/2011 | Koball et al. |
| 2011/0301472 A1 | 12/2011 | Grober et al. |
| 2012/0265116 A1* | 10/2012 | Szamosfalvi ....... A61M 1/3672 604/6.07 |
| 2013/0023776 A1* | 1/2013 | Olde .................. A61B 5/0215 600/487 |

FOREIGN PATENT DOCUMENTS

| | | |
|---|---|---|
| EP | 0 121 931 | 10/1984 |
| EP | 0 232 599 | 8/1987 |
| EP | 0 300 315 | 1/1989 |
| EP | 0 332 330 | 9/1989 |
| EP | 0330761 | 9/1989 |
| EP | 0 361 793 | 4/1990 |
| EP | 0 895 787 | 2/1999 |
| EP | 1 472 973 | 11/2004 |
| EP | 1 736 185 | 12/2006 |
| JP | 11104233 | 4/1999 |

(56) References Cited

FOREIGN PATENT DOCUMENTS

| | | |
|---|---|---|
| JP | 2005040518 | 2/2005 |
| JP | 2006/110118 | 4/2006 |
| JP | 2006/110120 | 4/2006 |
| WO | WO 91/00113 | 1/1991 |
| WO | 9710013 | 3/1997 |
| WO | WO 97/10013 | 3/1997 |
| WO | WO 99/29356 | 6/1999 |
| WO | WO 00/18451 | 4/2000 |
| WO | WO 02/102441 | 12/2002 |
| WO | WO 03/002174 | 1/2003 |
| WO | WO 03/006944 | 1/2003 |
| WO | WO 03/058567 | 1/2003 |
| WO | WO 03/058608 | 1/2003 |
| WO | WO 2005/019416 | 3/2005 |
| WO | WO 2006/122001 | 11/2006 |
| WO | 2007141246 | 12/2007 |
| WO | 2009127683 | 10/2009 |
| WO | 2009156174 | 12/2009 |
| WO | 2009156175 | 12/2009 |
| WO | 2010149726 | 12/2010 |
| WO | 2011080186 | 7/2011 |
| WO | 2011080188 | 7/2011 |
| WO | 2011080189 | 7/2011 |
| WO | 2013000777 | 1/2013 |

OTHER PUBLICATIONS

Brindley et al., "Predictors of survival following in-hospital adult cardiopulmonary resuscitation," Canadian Medical Association CMAJ, Aug. 20, 2002; 167 (4), pp. 343-348.
Bleyer et al., "Sudden and cardiac death rates in hemodialysis patients," Kidney International, vol. 55 (1999), pp. 1553-1559.
Karnik et al., "Cardiac arrest and sudden death in dialysis units," Kidney International, vol. 60 (2001), pp. 350-357.
Alpert, Sudden cardiac arrest and sudden cardiac death on dialysis: Epidemiology, evaluation, treatment, and prevention, Hemodialysis International 2011; 15 Suppl 1, pp. S22-S29.
Lindley et al., "Venous Needle Dislodgement Survey Dublin 2010" (ppt presentation) EDTNA/ERCA VND Project, presentation at EDTNA/ERCA 2011, Redsense medical, www.edtnaerca.org, 34 pages.
Guyton & Hall, "Textbook of Medical Physiology," 11th Edition, Elsevier Saunders, 2006, p. 155, ISBN-13: 978-0-7216-0240-0, 3 pages.
"Part 7.2: Management of Cardiac Arrest Circulation", Journal of the American Heart Association, Circulation 2005, Cover p. IV 58-66, downloaded from http://circ.ahajournals.org.
International Search Report—PCT/EP2014/055309 dated Jul. 1, 2014—4 pages.
U.S. Appl. No. 61/671,192.
U.S. Appl. No. 61/738,569.
Prosecution history of U.S. Appl. No. 13/001,314 (now U.S. Pat. No. 9,442,036), filed Dec. 23, 2010.
Prosecution history of U.S. Appl. No. 13/380,631 (now U.S. Pat. No. 9,433,356), filed Mar. 16, 2012.
Prosecution history of U.S. Appl. No. 14/129,087 (now U.S. Pat. No. 9,427,513), filed Apr. 11, 2014.
Prosecution history of U.S. Appl. No. 12/988,146 (now U.S. Pat. No. 8,718,957), filed Oct. 15, 2010.
Prosecution history of U.S. Appl. No. 13/000,856 (now U.S. Pat. No. 8,715,216), filed Dec. 22, 2010.
Prosecution history of U.S. Appl. No. 14/270,246 (now U.S. Pat. No. 9,383,288), filed May 5, 2014.
Prosecution history of U.S. Appl. No. 13/519,532, filed Sep. 12, 2012.
Prosecution history of U.S. Appl. No. 14/123,397, filed Dec. 2, 2013.
Prosecution history of U.S. Appl. No. 13/519,483, filed Sep. 13, 2012.
Prosecution history of U.S. Appl. No. 13/519,559, filed Sep. 12, 2012.
Prosecution history of U.S. Appl. No. 14/234,527, filed May 5, 2014.
Prosecution history of U.S. Appl. No. 14/408,849, filed Dec. 17, 2014.
Prosecution history of U.S. Appl. No. 14/651,730, filed Jun. 12, 2015.
Prosecution history of U.S. Appl. No. 14/917,099, filed Mar. 7, 2016.
Prosecution history of U.S. Appl. No. 15/104,861, filed Jun. 15, 2016.
Wabel et al., Ansätze zur Identifikation von Patientenparametern während der Hämodialysetherapie, Identification of Patient Parameters during Hemodialysis, vol. 50, Issue May 2002 (May 2002) pp. 220-227 ISSN (Print) 0178-2312, Published Online Sep. 25, 2009—English Translation—11 pages.

* cited by examiner

MONITORING OF CARDIAC ARREST IN A PATIENT CONNECTED TO AN EXTRACORPOREAL BLOOD PROCESSING APPARATUS

CROSS-REFERENCE TO RELATED APPLICATIONS

The present application is a National Phase of International Application No. PCT/EP2014/055309, filed on Mar. 17, 2014, which claims priority to Sweden Patent Application No. 1350344-6, filed Mar. 20, 2013, the entire contents of each of which are incorporated herein by reference and relied upon.

TECHNICAL FIELD

The present invention generally relates to techniques for detecting and signaling cardiac arrest in a patient subjected to extracorporeal blood processing, e.g. using a dialysis machine.

BACKGROUND ART

In extracorporeal blood processing, blood is taken out of a human or animal subject, processed (e.g. treated) and then reintroduced into the subject by means of an extracorporeal blood flow circuit ("EC circuit") which is part of a blood processing apparatus. Generally, the blood is circulated through the EC circuit by a blood pump. In certain types of extracorporeal blood processing, the EC circuit includes an access device for blood withdrawal (e.g. an arterial needle or catheter) and an access device for blood reintroduction (e.g. a venous needle or catheter), which are inserted into a dedicated blood vessel access (e.g. fistula or graft) on the subject. Such extracorporeal blood treatments include hemodialysis, hemodiafiltration, hemofiltration, plasmapheresis, bloodbanking, blood fraction separation (e.g. cells) of donor blood, apheresis, extracorporeal blood oxygenation, assisted blood circulation, extracorporeal liver support/dialysis, ultrafiltration, etc.

It is vital to minimize the risk for malfunctions in the EC circuit, since these may lead to a potentially life-threatening condition of the subject. Serious conditions may e.g. arise if the EC circuit is disrupted downstream of the blood pump, e.g. by a Venous Needle Dislodgement (VND) event, in which the venous needle comes loose from the blood vessel access. Such a disruption may cause the subject to be drained of blood within minutes. Much research has been devoted to preventing and detecting VND, e.g. by improving the attachment of the needle and the associated tubing to the patient, by installing dedicated external equipment for detecting leakage of blood at the blood vessel access, or by monitoring the pressure measured by a pressure sensor ("venous pressure sensor") on the downstream side of the blood pump in the EC circuit. Conventionally, the pressure monitoring is carried out by comparing one or more measured static pressure levels with one or more threshold values. However, it may be difficult to set appropriate threshold values, since the static pressure in the EC blood circuit may vary between treatments, and also during a treatment, e.g. as a result of the subject moving. Further, if the venous needle comes loose and gets stuck in bed sheets or the subject's clothes, the measured static pressure level might not change enough to indicate the potentially dangerous situation. To overcome these drawbacks WO97/10013, US2005/0010118, WO2009/156174, WO2010/149726 and US2010/0234786 all propose various techniques for detecting a VND event by identifying an absence of heart or breathing pulses in a pressure signal from a pressure sensor on the downstream side of the blood pump in the EC circuit.

Even if VND is a serious intradialytic complication, it is much less common than cardiac arrest, also known as cardiopulmonary arrest or circulatory arrest, which is the cessation of normal circulation of the blood due to failure of the heart to contract effectively. In 1999, the article "Sudden and cardiac death rates in hemodialysis patients" by Bleyer et al, published in *Kidney International*, Vol. 55 (1999), pp. 1553-1559, reported on an increased sudden and cardiac death rate for hemodialysis patients in the US. This utterly severe intradialytic complication has later been reported to occur in about 7 out of 100 000 treatments, which is about 5-10 times more common that VND, see the article "Cardiac arrest and sudden death in dialysis units" by Karnik et al, published in *Kidney Int.* 2001 July; 60(1):350-7. Based on the fact that about 150 treatments are performed annually for each patient among a global total of 2 million patients, it can be assumed that about 20 000 incidents of cardiac arrest occur during ongoing dialysis worldwide each year. The outcome of a cardiac arrest event for a dialysis patient is generally very poor: 13% of the patients die in the clinic in connection with the treatment and 60% die within 48 hours, as reported by Karnik et al. As noted by Alpert in the article "Sudden cardiac arrest and sudden cardiac death on dialysis: Epidemiology, evaluation, treatment, and prevention", published in *Hemodial Int*, 2011 October; 15 *Suppl* 1:822-9, sudden cardiac arrest is the most common cause of death in dialysis patients.

According to Sasson et al in the article "Predictors of survival from out-of-hospital cardiac arrest: a systematic review and meta-analysis", published in *Circ Cardiovasc Qual Outcomes* 2010, 3:63-81, only 8% of all persons with cardiac arrest survive after being given cardio-pulmonary resuscitation (CPR). Incidents taking place in a clinical environment have a better outcome, with a survival rate of 22% of witnessed cardiac arrests, as reported by Peter et al in the article "Predictors of survival following in-hospital adult cardiopulmonary resuscitation", published in *CMAJ* 2002; 167(4):343-8. CPR alone is unlikely to restart the heart, but provision of an electric shock to the subject's heart (defibrillation) is usually needed in order to restore a viable or "perfusing" heart rhythm.

As to morbidity, about 50% of persons that had cardiac arrest for 5 to 8 minutes will suffer from brain damage after successful revival, according to Guyton & Hall, "Textbook of Medical Physiology", 11th edition, Elsevier Saunders, 2006, page 155, ISBN-13: 978-0-7216-0240-0. CPR is only likely to be effective if commenced within 6 minutes after the heart stops beating because permanent brain cell damage occurs when fresh blood infuses the cells after that time. The cells of the brain become dormant in as little as 4-6 minutes in an oxygen deprived environment, and the cells are unable to survive the reintroduction of oxygen in a traditional resuscitation. In summary, fast detection and early cardio-pulmonary resuscitation (CPR) followed by defibrillation is crucial for a successful outcome.

In many dialysis clinics, the staff cannot provide constant supervision of their patients from this point of view. According to a survey conducted with 385 nurses from 39 countries, as reported by E Lindley in "Venous Needle Dislodgement Survey Dublin 2010", EDTNA/ERCA VND Project, presentation at EDTNA/ERCA 2011, 58% of the respondents claimed that there are patients in their clinics who are not clearly visible from the nurse's station. 70% stated that the patients are regularly checked, but at long intervals, usually of 30 to 60 minutes. It can be concluded that there is a high risk for cardiac arrest events to pass unnoticed for such a long time that there is no reasonable likelihood of saving the patient from damage or death.

For economic and practical reasons it is undesirable to connect all dialysis patients to dedicated equipment for detecting and signaling cardiac arrest, such as a pulse watch or an electrocardiograph (ECG).

Even if it has been known for a long time to monitor heart pulses in the pressure signal from a venous pressure sensor in a dialysis machine for the purpose of detecting VND, no one has so far suggested detecting and signaling cardiac arrest based on a pressure signal from a pressure sensor in the dialysis machine. It has been suggested to monitor the heart rate in conjunction with VND, e.g. in EP0330761, US2005/0010118 and WO2009/156175, but this does not imply that the heart rate is used or even may be used for the purpose of detecting cardiac arrest. It should be understood that outputting a signal that truly represents the heart rate is not a trivial task, especially when the heart rate disappears or the heart pulses become very weak. During dialysis treatment, the blood pump is running and creates strong pulsations in the pressure signal, especially if the blood pump is of the normal, peristaltic type. It is not uncommon for the pulsations from the pump to be much stronger than the pulsations from the heart in the pressure signal. Even if filtering may be employed for suppressing the pulsations from the pump, such filtering is normally incomplete, leaving at least weak residuals of the pulsations from the pump in the filtered pressure signal. This means that if the heart stops, the algorithm or circuitry for extracting the heart rate is likely to identify the residuals and still output a frequency signal in the region of a normal heart rate (since the blood pump is normally running at a frequency within the frequency range of heartbeats). All in all, this means that it cannot be surmised that the prior art implies a technique for detecting cardiac arrest given a mere reference to an ability to detect the heart rate in a pressure signal.

Clearly, there is a long-felt but unmet need in the field of hemodialysis for a simple and cost-effective technique of on-line monitoring for cardiac arrest in dialysis patients during dialysis treatment. This need has been known at least since the late 1990s, and while it was suggested already in 1988, in aforesaid EP0330761, to monitor the heart rate using the pressure signal from a pressure sensor in an EC circuit, no one has made the connection that cardiac arrest could be monitored via such a pressure signal.

SUMMARY

It is an objective of the invention to at least partly overcome one or more of the above-identified limitations of the prior art.

Another objective is to provide a technique for monitoring of cardiac arrest in a patient connected to an extracorporeal blood processing apparatus.

Yet another objective is to provide such a monitoring technique which is cheap and simple to implement.

A further objective is to provide such a monitoring technique which has a low occurrence of false positives and false negatives.

One or more of these objectives, as well as further objectives that may appear from the description below, are at least partly achieved by means of monitoring devices, apparatus for extracorporeal blood processing, a monitoring method and a computer-readable medium according to the independent claims, embodiments thereof being defined by the dependent claims.

A first aspect of the invention is a monitoring device, which comprises an input block configured to obtain a first pressure signal from a first pressure sensor, which is arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and comprises at least one blood pumping device operable to pump blood from the vascular system through the blood processing unit and back to the vascular system; a processing block configured to repeatedly process the first pressure signal for generation of a time-sequence of parameter values indicative of pressure pulsations originating from heartbeats in the subject; and an evaluation block configured to evaluate the parameter values according to a detection criterion for cardiac arrest, which is set to detect a disappearance of the pressure pulsations originating from the heartbeats in the first pressure signal, and, if the detection criterion is fulfilled, generate an alarm signal that signals a cardiac arrest in the subject.

In one embodiment, the input block is further configured to obtain a second pressure signal from a second pressure sensor, which is arranged in the extracorporeal blood processing apparatus to detect pressure variations in the fluid, wherein the processing block is configured to process the first and the second pressure signals for generation of the time-sequence of parameter values. The detection criterion for cardiac arrest may set to detect a disappearance of the pressure pulsations originating from the heartbeats in both of the first and second pressure signals.

In one embodiment, the time-sequence of parameter values comprises a time-sequence of first rate values that represent a rate of the pressure pulsations originating from the heartbeats in the first pressure signal, and a time-sequence of second rate values that represent a rate of the pressure pulsations originating from the heartbeats in the second pressure signal, wherein the detection criterion involves identifying a difference between the first and second rate values.

In one embodiment, the time-sequence of parameter values comprises a time-sequence of correlation values that represent a degree of correlation between the first and second pressure signals, wherein the detection criterion involves comparing the correlation values to a correlation threshold.

In one embodiment, the time-sequence of parameter values comprises a time-sequence of magnitude values that represent a magnitude of the pressure pulsations originating from the heartbeats in at least the first pressure signal, wherein the detection criterion involves comparing the magnitude values to a magnitude threshold.

In one embodiment, the time-sequence of parameter values comprises a time-sequence of rate values that represent a rate of the pressure pulsations originating from the heartbeats in at least the first pressure signal, wherein the detection criterion involves at least one of: identifying a sudden change in the time-sequence of rate values; identifying, based on the time-sequence of rate values, that the rate of the pressure pulsations is substantially equal to a frequency of said at least one blood pumping device; and identifying, based on the time-sequence of rate values, that the rate of pressure pulsations is outside a predefined range, which preferably defines physiological limits for the rate of heartbeats in the subject.

In one embodiment, the time-sequence of the parameter values comprises a time-sequence of statistical values that represent the shape of at least the first pressure signal and are computed as a statistical measure for signal values within a time window in at least the first pressure signal, wherein the detection criterion involves comparing the statistical values to a statistics threshold.

In one embodiment, the evaluation block comprises a detection test sub-block and a verification test sub-block, wherein the monitoring device is configured to, during operation of said at least one blood pumping device, cause the detection test sub-block to evaluate the time-sequence of parameter values according to the detection criterion, and wherein the monitoring device is configured to, if the detection criterion is fulfilled, stop said at least one blood pumping device and initiate the verification test sub-block, and wherein the verification test sub-block is configured to, upon said initiation, evaluate at least the first pressure signal for absence of the pressure pulsations originating from heartbeats in the subject when said at least one blood pumping device is stopped and, upon detection of absence of the pressure pulsations, cause the evaluation block to generate the alarm signal that signals a cardiac arrest in the subject.

In one embodiment, the verification test sub-block is configured to evaluate at least the first pressure signal for absence of the pressure pulsations originating from heartbeats in the subject based on the time sequence of parameter values that are generated by the processing block after said at least one blood pumping device has been stopped.

In one embodiment, the input block is configured to perform a preparatory filtering to suppress pressure pulsations that originate from said at least one blood pumping device in at least the first pressure signal, wherein the monitoring device is configured to change or disable the preparatory filtering in the input block when the verification test sub-block is initiated.

In one embodiment, the detection test sub-block is further configured to, if the detection criterion is fulfilled, evaluate a confidence level of the thus-fulfilled detection criterion, wherein the detection test sub-block is configured to cause the evaluation block to generate the alarm signal if the confidence level is deemed sufficient, and wherein the monitoring device is configured to initiate the verification test sub-block if the confidence level is deemed insufficient.

In one embodiment, the verification test sub-block is configured to, if being unable to detect absence of the pressure pulsations in at least the first pressure signal, initiate a configuration process for setting the detection criterion based on at least the first pressure signal.

In one embodiment, the monitoring device is operable in a viability checking phase to enable the monitoring device for detection of cardiac arrest, wherein the viability checking phase comprises: comparing a magnitude of the pressure pulsations that originate from the heartbeats in at least the first pressure signal to a viability threshold; and enabling the monitoring device for detection of cardiac arrest provided that the magnitude exceeds the viability threshold.

In one embodiment, the viability checking phase further comprises selecting at least the first pressure signal among a plurality of pressure signals obtained from a plurality of pressure sensors in the extracorporeal blood processing apparatus, based on the magnitude of the pressure pulsations originating from the heartbeats in the respective pressure signal.

In one embodiment, the monitoring device is configured to perform the viability checking phase such that said at least one blood pumping device is stopped during at least part of the viability checking phase.

In one embodiment, the extracorporeal blood processing apparatus is connected to the vascular system via a single access device and is configured to operate in a repeating sequence of a blood withdrawal period in which a first blood pumping device is operated to draw blood from the vascular system via the access device, a blood return period in which a second blood pumping device is operated to the pump blood back to the vascular system via the access device, and a switching period between the withdrawal and blood return periods in which the first and second blood pumping devices are stopped, wherein the processing block is configured to generate the time-sequence of parameter values during the switching period, and wherein the evaluation block is configured to evaluate the parameter values generated during the switching period for detection of cardiac arrest.

In another embodiment, the extracorporeal blood processing apparatus is connected to the vascular system via a single access device and is configured to operate in a repeating sequence of a blood withdrawal period in which said at least one blood pumping device is operated to draw blood from the vascular system via the access device into a container, a blood return period in which said at least one blood pumping device is stopped and the blood flows from the container back into the vascular system via the access device, and wherein the processing block is configured to generate the time-sequence of parameter values during the blood return period, and wherein the evaluation block is configured to evaluate the parameter values generated during the blood return period for detection of cardiac arrest.

In one embodiment, the monitoring device is configured to modify the detection criterion as a function of one or more operating parameters of the extracorporeal blood processing apparatus, such as a pumping rate of said at least one blood pumping device.

In one embodiment, the first pressure sensor is arranged upstream of the blood processing unit and said at least one blood pumping device in an extracorporeal blood circuit in the extracorporeal blood processing apparatus, and wherein the pressure pulsations originating from heartbeats in the subject are superimposed on a baseline pressure level in the first pressure signal, wherein the evaluation block is configured to generate the alarm signal only in absence of a recent change in the baseline pressure level.

In one embodiment, the first pressure sensor is one of a pressure sensor arranged downstream of said at least one blood pumping device and the blood processing unit in an extracorporeal blood circuit in the extracorporeal blood processing apparatus, a pressure sensor arranged upstream of said at least one blood pumping device and the blood processing unit in the extracorporeal blood circuit, and a pressure sensor arranged in a treatment fluid supply system for pumping a treatment fluid through the blood processing unit.

A second aspect of the invention is a monitoring device, which comprises: means for obtaining a first pressure signal from a first pressure sensor, which is arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and comprises at least one blood pumping device operable to pump blood from the vascular system through the blood processing unit and back to the vascular system; means for repeatedly processing the first pressure signal for generation of a time-sequence of parameter values indicative of pressure pulsations originating from heartbeats in the subject; means for evaluating the parameter values according to a detection criterion for cardiac arrest, which is set to detect a disappearance of the pressure pulsations originating from the heartbeats in the first pressure signal; and means for generating, if the detection criterion is fulfilled, an alarm signal that signal a cardiac arrest in the subject.

A third aspect of the invention is a monitoring device, which comprises: an input block configured to obtain a first pressure signal from a first pressure sensor, which is arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and comprises at least one blood pumping device operable to pump blood from the vascular system through the blood processing unit and back to the vascular system; and a signal processor configured to repeatedly process the first pressure signal for generation of a time-sequence of parameter values indicative of pressure pulsations originating from heartbeats in the subject; to evaluate the parameter values according to a detection criterion for cardiac arrest, which is set to detect a disappearance of the pressure pulsations originating from the heartbeats in the first pressure signal, and generate, if the detection criterion is fulfilled, an alarm signal that signals a cardiac arrest in the subject.

A fourth aspect of the invention is an apparatus for extracorporeal blood processing, which comprises an extracorporeal blood circuit for connection to the vascular system of a subject; a blood processing unit in the extracorporeal blood circuit; at least one blood pumping device in the extracorporeal blood circuit operable to pump blood from the vascular system through the blood processing unit and back to the vascular system; a treatment fluid supply system operable to pump a treatment fluid through the blood processing unit; a pressure sensor arranged in one of the extracorporeal blood circuit and the treatment fluid supply system to detect pressure variations in one of the blood and the treatment fluid; and a pressure sensor arranged in one of the extracorporeal blood circuit and the treatment fluid supply system to detect pressure variations in one of the blood and the treatment fluid; wherein the apparatus further comprises a monitoring device according to any one of the first to third aspects.

In one embodiment, the apparatus further comprises revival equipment for cardiopulmonary resuscitation and/or defibrillation. The apparatus may be operable to activate the revival equipment when the monitoring device has generated the alarm signal that signals a cardiac arrest in the subject. Alternatively or additionally, the apparatus may be operable to control the treatment fluid supply system to decrease the temperature of the treatment fluid, so as to decrease the body temperature of the subject, when the monitoring device has generated the alarm signal that signals a cardiac arrest in the subject.

In one embodiment, the apparatus is operable to control, when the monitoring device has generated the alarm signal that signals a cardiac arrest in the subject, at least one of the treatment fluid supply system and the extracorporeal blood circuit to change the composition of the blood pumped to the vascular system of the subject. The dialysis machine may change the composition of the treatment fluid, which indirectly affects the composition of the blood pumped to the patient, or directly change the composition of the blood pumped to the patient, e.g. by injection into the blood. The change of composition may involve adding a new substance or increasing/decreasing the amount of an existing substance. The substance may be selected in the group comprising vasopressors, epinephrine, vasopressin, atropine, amiodarone, lidocaine, saline solution, calcium chloride, sodium chloride, calcium gluconate, citrate, heparin, potassium, magnesium, glucose, bicarbonate, oxygen and carbon dioxide.

A fifth aspect of the invention is a monitoring method, which comprises: obtaining a first pressure signal from a first pressure sensor, which is arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and comprises at least one blood pumping device operable to pump blood from the vascular system through the blood processing unit and back to the vascular system; processing the first pressure signal for generation of a time-sequence of parameter values indicative of pressure pulsations originating from heartbeats in the subject; evaluating the parameter values according to a detection criterion for cardiac arrest, which is set to detect a disappearance of the pressure pulsations originating from the heartbeats in the first pressure signal; and generating, if the detection criterion is fulfilled, an alarm signal that signals a cardiac arrest in the subject.

A sixth aspect of the invention is a computer-readable medium comprising computer instructions which, when executed by a processor, cause the processor to perform the method according to the fifth aspect.

Any one of the above-identified embodiments of the first aspect may be adapted and implemented as an embodiment of the second to sixth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

Figure 1:
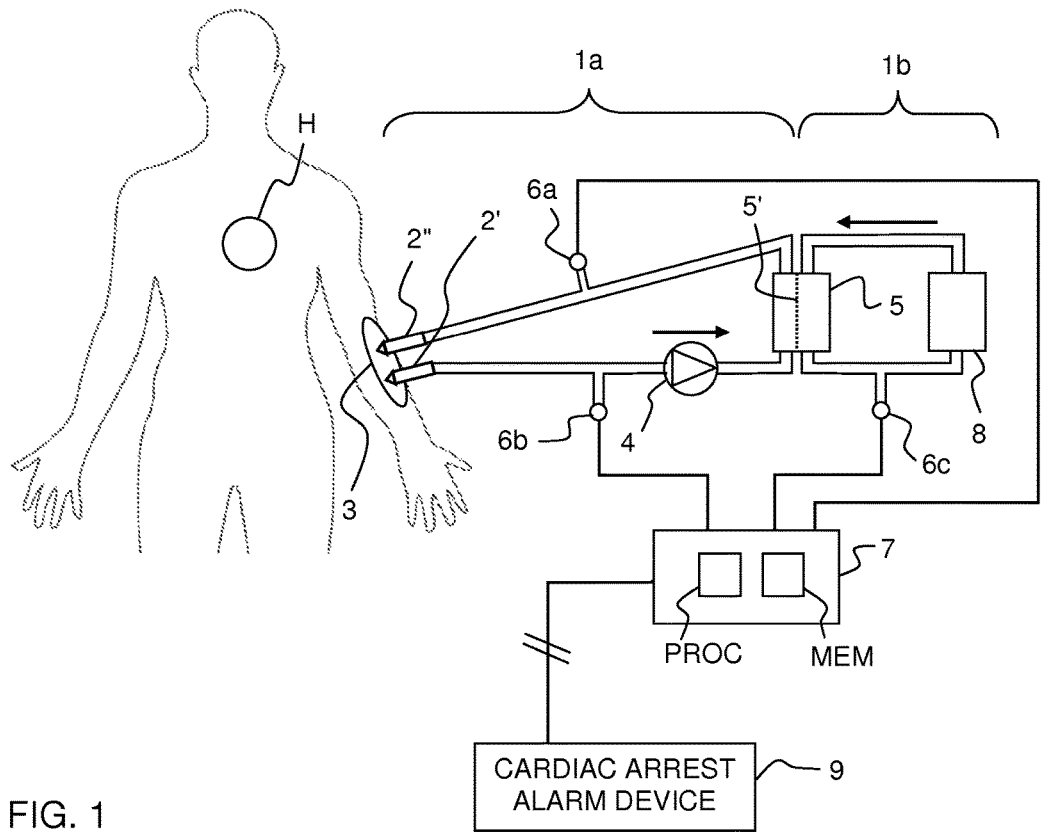
FIG. 1 a schematic diagram of an extracorporeal blood treatment apparatus attached to a human subject.

Before describing embodiments of the invention, a few definitions will be given.

As used herein, "cardiac arrest" refers to a sudden, unexpected loss of heart function, i.e. that the heart stops beating. It is also commonly known as "sudden cardiac arrest", "cardiopulmonary arrest" or "circulatory arrest".

As used herein, a "magnitude" is generally representative of the strength of a heart pulse and may be given by any magnitude measure. The magnitude may be estimated in the time domain and be given by, e.g., the amplitude of the heart pulse, a sum of the pressure values that form the heart pulse (where the pressure values may, but need not, be absolute values), or an energy/power measure for the heart pulse, such as the sum of squares, the variance or the standard deviation for the pressure values that form the heart pulse. The magnitude may be estimated for an individual heart pulse or for a sequence of heart pulses (e.g. as an average) in a pressure signal. The individual heart pulses may be detected using any available technique, such as peak detection, zero crossing detection, shape or derivative analysis, template matching, etc. It is also conceivable to omit the step of detecting individual heart pulses in the pressure signal, and instead compute the magnitude measure for all pressure values within a time window of predetermined length (that exceeds the maximum expected time difference between consecutive heart pulses) in the pressure signal. The magnitude may alternatively be estimated in the frequency domain by computing the energy or power distribution across frequencies for the signal values within a time window in the pressure signal, e.g. using any available Power Spectral Density (PSD) method, parametric or non-parametric, such as a Fourier transformation method, e.g. FFT. The magnitude may be given by a peak value in a spectral diagram generated by the frequency domain analysis. The magnitude may also be estimated by combining the results from a time domain method and a frequency domain method.

As used herein, a "heart rate" is generally representative of the pulse repetition rate of heart pulses in the respective pressure signal and may be given as a number of pulses per unit time. The heart rate may be estimated in the time domain and be given by the inverse of a time difference between heart pulses (also known as RR intervals in the field of electrocardiography, ECG) detected in the respective pressure signal. The RR interval may be the time interval between consecutive heart pulses or an average of such time intervals within a time window in the pressure signal. As used herein, the term "heart rate" is intended to also include its inverse, i.e. the (average) time interval between consecutive heart pulses. The heart rate may alternatively be estimated in the frequency domain and may e.g. be given by the frequency of the peak value in the above-mentioned spectral diagram. The heart rate may also be estimated by combining the results from a time domain method and a frequency domain method.

All of the above-mentioned techniques for magnitude and heart rate estimation, and alternatives and variants thereof, are well-known to the skilled person.

As used herein, an estimated magnitude or rate of heart pulses in a pressure signal refers to an apparent magnitude or rate of heart pulses, i.e. the magnitude or rate of pulses in the pressure signal is estimated under the assumption that these pulses are heart pulses. There is no explicit knowledge that there actually are any heart pulses in the pressure signal when the magnitude or rate is estimated.

Throughout the description, the same reference numerals are used to identify corresponding elements.

Embodiments of the invention will be exemplified with reference to an apparatus for blood treatment, which is schematically depicted in FIG. 1. In the following example, the apparatus is assumed to be a dialysis system which is formed by a blood line set attached to a dialysis machine or monitor, as is well known in the art. FIG. 1 illustrates a human subject or patient which is connected to an extracorporeal blood flow circuit 1a by way of access devices 2', 2" inserted into a dedicated vascular access 3 (also known as "blood vessel access") on the patient. The extracorporeal blood flow circuit 1a (denoted "EC circuit" in the following) is configured to communicate blood to and from the cardiovascular system of the patient. In the illustrated example, a blood pump 4 draws blood from the vascular access 3 via access device 2' and pumps the blood through a blood treatment unit 5 and back to the vascular access 3 via access device 2". Thus, when both access devices 2', 2" are connected to the vascular access 3, the EC circuit 1a defines a blood path that starts and ends at the vascular access 3. The EC circuit 1a may be seen to comprise a "venous side" which is the part of the blood path located downstream of the blood pump 4, and an "arterial side" which is the part of the blood path located upstream of the blood pump 4. The blood pump 4 may be of any type, e.g. a rotary peristaltic pump, a linear peristaltic pump, a diaphragm pump, or a centrifugal pump.

The blood treatment unit 5 may be any type of blood filtration device, such as a coil dialyzer, a parallel plate dialyzer, a hollow fiber dialyzer, etc. For simplicity, the blood treatment unit 5 is denoted "dialyzer" in the following. The dialyzer 5 has a blood side and a treatment fluid side separated by a semipermeable membrane 5'. The blood side is connected as part of the EC circuit 1a, and the treatment fluid side is connected as part of a supply system for treatment fluid 1b (denoted "TF circuit" in the following). The TF circuit 1b is arranged to pump a treatment fluid through the treatment fluid side of the dialyzer 5, whereby solutes are transported over the membrane 5' due to a concentration gradient and/or ultrafiltrate is transported over the membrane 5' due to a pressure gradient. The skilled person understands that the TF circuit 1b may include a plurality of functional components such as a source of fresh treatment fluid, a receptacle/drain for spent treatment fluid, one or more pumps, balancing chambers, valves, heaters, conductivity sensors, etc. For simplicity, these components are collectively represented by a generic box 8 in FIG. 1.

It is understood that the EC circuit 1a and the TF circuit 1b form part of the above-mentioned apparatus for blood treatment.

The EC circuit 1a includes a pressure sensor or transducer 6a on the venous side of the EC circuit 1a, downstream of the dialyzer 5 (denoted "venous pressure sensor" or "venous sensor"), a pressure sensor or transducer 6b on the arterial side of the EC circuit 1a (denoted "arterial pressure sensor" or "arterial sensor"). The venous and arterial sensors 6a, 6b provide a respective time-varying signal that represents the pressure in the blood on the venous side ("venous signal") and the arterial side ("arterial signal"), respectively. In the following, the venous signal is denoted p6a and the arterial signal is denoted p6b.

Furthermore, a pressure sensor or transducer 6c (denoted "TF pressure sensor" or "TF sensor") is arranged in the TF circuit 1b to provide a time-varying signal that represents the pressure in the treatment fluid ("TF signal"). The TF signal is denoted p6c in the following. The TF sensor 6c may have any placement in the TF circuit 1b, e.g. downstream of the dialyzer 5, as shown in FIG. 1, or upstream of the dialyzer 5, as shown in FIG. 6.

A monitoring device 7 is connected to the sensors 6a, 6b, 6c by way of a respective data line to acquire and process the time-varying electric signals p6a, p6b, p6c. The monitoring device 7 may be included as part of the apparatus for blood treatment, e.g. in the above-mentioned dialysis machine. Specifically, the monitoring device 7 comprises processing circuitry configured to process the signals p6a-p6c, during ongoing blood treatment, for the purpose of monitoring the patient for occurrence of cardiac arrest (CA). The CA monitoring is based on detection of heart activity in one or more of the pressure signals p6a-p6c. The heart activity is manifested by presence of "heart pulses" in the respective pressure signal. A "pulse" is a set of data samples that defines a local increase or decrease (depending on implementation) in signal magnitude within a time-dependent signal. The "heart pulses" represent pressure waves that are generated by the beating of the heart H ("heartbeats") in the subject and propagate through the cardiovascular system of the subject to the vascular access 3. These pressure waves may enter the venous side of the EC circuit 1a via the access device 2" and reach the venous sensor 6a, which produces corresponding heart pulses in the venous signal p6a. The pressure waves may also enter the arterial side of the EC circuit 1a via the access device 2' and reach the arterial sensor 6b, which also produces corresponding heart pulses in the arterial signal p6b. Generally, the heart pulses appear at a rate proportional to the beat rate of the heart H. The magnitude, shape and timing of the heart pulses may differ between the venous and arterial signals p6a, p6b. Depending on the configuration of the EC circuit 1a, the dialyzer 5 and the TF circuit 1b, the pressure waves may also reach the TF sensor 6c, which then produces corresponding heart pulses in the TF signal p6c. As used herein, a "pressure wave" is a mechanical wave in the form of a disturbance that travels or propagates through a material or substance. In the context of the following examples, the pressure waves propagate in the cardiovascular system of the subject, the blood path of the EC circuit 1a and the TF circuit 1b at a velocity that typically lies in the range of about 3-50 m/s.

Figure 3A:
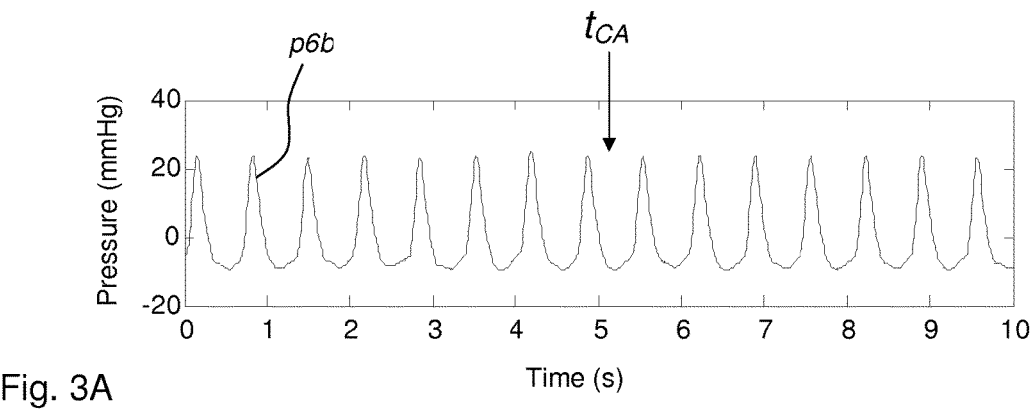
FIGS. 3A-3C are examples of time-varying signals retrieved from an arterial pressure sensor in the apparatus in FIG. 1 and used in the inventive CA monitoring.
Figure 4A:
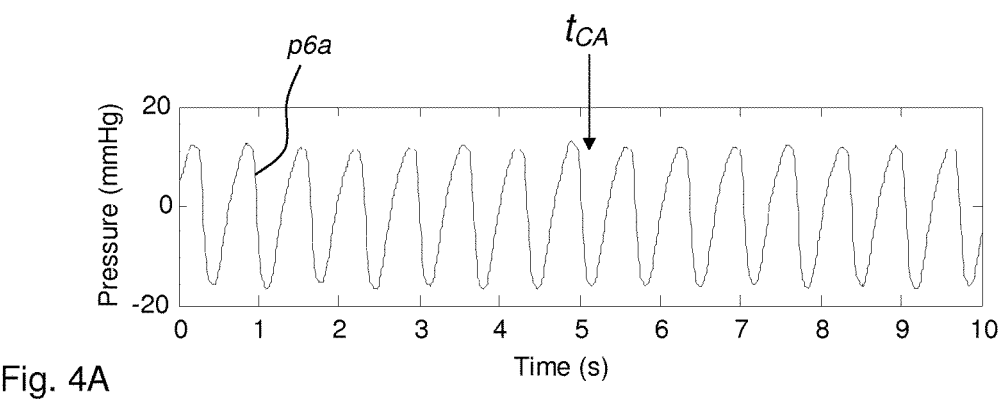
FIGS. 4A-4C are examples of time-varying signals retrieved from a venous pressure sensor in the apparatus in FIG. 1 and used in the inventive CA monitoring.

Generally, the sensors 6a-6c do not only measure heart pulses, but also various disturbances caused by pressure variations in the blood and the treatment fluid at the respective sensor 6a-6c. The disturbances may include both periodic and non-periodic components, and they may originate from the patient, from the EC circuit 1a and from the TF circuit 1b. Non-periodic disturbances may e.g. be caused by the patient moving or by non-periodic phenomena in the patient, such as hiccups, sneezing, vomiting, etc. Periodic disturbances may originate from periodic phenomena in the patient, such as breathing. Pumps, valves, clamps etc in the EC circuit 1a and the TF circuit 1b may cause non-periodic and periodic disturbances. For example, during ongoing treatment, the blood pump 4 is known to generate strong, periodic disturbances ("pump pulses") in all of the signals p6a-p6c. As is well known in the art, the pump pulses contain plural frequency components, including a basic frequency of the blood pump and harmonics of the basic frequency. Generally, the disturbances make it difficult to detect the heart pulses. FIG. 3A illustrates an arterial signal p6b which is acquired during treatment when the blood pump 4 is operated to generate a blood flow rate of 400 ml/min in the EC circuit 1a. The arterial signal p6b includes pump pulses and heart pulses with an approximate magnitude ratio of 30:1. The heart pulses occur at a rate of 75 beats per minute (bpm). A CA incident occurs at the location of the arrow $t_{CA}$. As seen, it is difficult to detect that the heart pulses disappear at this time point in the arterial signal p6b. FIG. 4A illustrates a venous signal p6a acquired during the same treatment, and the disappearance of heart pulses at time at time $t_{CA}$ is likewise difficult to detect in this signal.

Figure 3B:
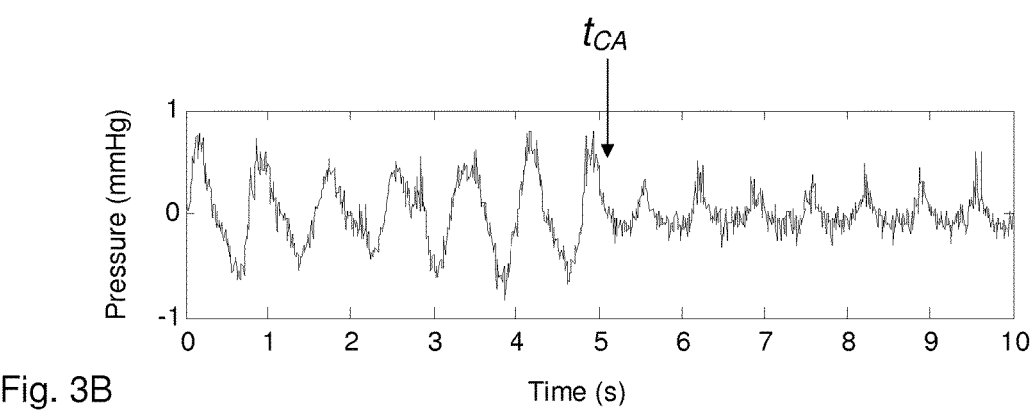
Figure 4B:
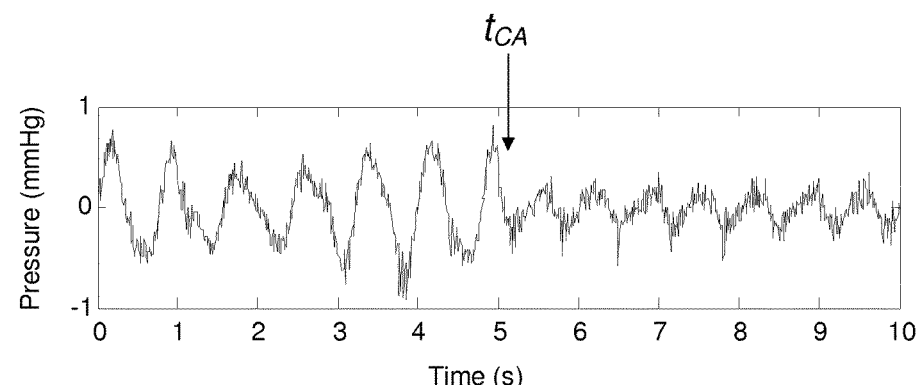

To facilitate detection of the heart pulses, the monitoring device 7 may be adapted to filter the pressure signals p6a-p6c for removal or suppression of the disturbances. Any known filtering technique may be used, e.g. any one of the techniques disclosed in WO2009/156175, US2005/0010118, WO2010/149726, WO2013/000777, as well as in Applicant's U.S. provisional patent application No. 61/671,192, entitled "FILTERING OF PRESSURE SIGNALS FOR SUPPRESSION OF PERIODIC PULSES", which was filed on Jul. 13, 2012, and Applicant's U.S. provisional patent application No. 61/738,569, entitled "DETECTING PRESSURE PULSES IN A BLOOD PROCESSING APPARATUS", which was filed on Dec. 18, 2012. FIG. 3B illustrates the arterial signal p6b in FIG. 3A after filtering, and FIG. 4B illustrates the venous signal p6a in FIG. 4A after filtering. The heart pulses are clearly visible, and the disappearance of the heart pulses at time $t_{CA}$ is identifiable. However, the filtering is not perfect, and residuals of the disturbances remain in the respective filtered signal, as seen from the pulsations that remain in the filtered signal after the time point $t_{CA}$. The magnitude and frequency content of the residuals may vary over time, and may intermittently make it difficult to detect the heart pulses and/or have significant impact of the evaluation parameter(s) that are used in the CA monitoring (see below). For example, the filtered signal may be temporarily dominated by the disturbances e.g. when the patient moves, sneezes, etc, or when the operating condition of the dialysis machine is changed, e.g. when the pumping rate of the blood pump is modified. Further, depending on filtering technique, the residuals may increase in magnitude when the basic frequency of the blood pump (or one of its harmonics) happen to coincide with the heart rate.

It is to be understood that the EC circuit 1a and/or TF circuit 1b may include further pressure sensors (not shown) that provide a respective pressure signal that may be connected to the monitoring device 7 and processed for detection of a CA incident.

When the monitoring device 7 concludes that a CA incident has occurred, it generates a dedicated CA alarm signal. The CA alarm signal may result in an audible and/or visible alarm, which is generated by one or more alarm devices 9 (one shown in FIG. 1) which may be arranged in or at the blood treatment apparatus and/or in a remote location. It should be noted that the CA alarm signal is a dedicated signal, which is distinct from any other general or specific alarm signals that may be generated by other monitoring devices or control systems arranged in or associated with the blood treatment apparatus. For example, it is well-known in the art that dialysis machines may include safety systems that indicate a Venous Needle Dislodgement (VND detector), presence of air in the blood in the EC circuit 1*a* (air detectors), blood leakage into the TF circuit 1*b* via the dialyzer 5 (blood leakage detectors), etc. The dedicated CA alarm signal is suitably connected to the alarm device 9 to result in an equally dedicated CA alarm to specifically alert the staff responsible for the blood treatment about the occurrence of the CA incident. Thereby, the staff is alerted to immediately check the patient's pulse and if it has disappeared start reviving the patient by CPR and defibrillation.

At many dialysis clinics, the staff needs to call upon a special emergency team in order to start CPR and defibrillation. Since time is critical, the dialysis machine may be equipped with a defibrillator so that the clinical staff does not have to wait for the emergency team to arrive. If the staff lacks adequate training or skills to perform CPR or defibrillation, the dialysis machine may be configured to, upon generation of the CA alarm signal, give relevant instructions or guidance for revival of the patient, e.g. via a built-in display or speaker on the dialysis machine, either automatically or on command, e.g. by the staff pushing a dedicated button on the machine. For unattended patients that are connected to revival equipment for automated CPR and/or defibrillation, it is conceivable that the monitoring device 7 in addition to generating the CA alarm signal is arranged to trigger the revival equipment to initiate the automated CPR and/or defibrillation.

As a further feature, in all embodiments disclosed herein, the dialysis machine may be configured to induce therapeutic hypothermia, i.e. to lower the body temperature of the patient, upon generation of the CA alarm signal. It has become a common practice of emergency clinics to cool the body of patient after a cardiac arrest to protect a blood-starved brain and heart, e.g. from the rush of oxygen that comes with the resumption of normal cardiac rhythms. Much time and effort can be saved if the dialysis machine is operable to cool the dialysis patient after detection of a cardiac arrest. Cooling can thereby be initiated at the dialysis clinic, rather than at an emergency clinic at a much later time. Accordingly, the dialysis machine may be configured to reduce the temperature of the treatment fluid, either automatically or on command, e.g. by the staff pushing a dedicated button on the machine, following the generation of a CA alarm signal by the monitoring device 7. The dialysis machine may thereby cool the patient to temperatures below 35° C., e.g. in the range of 30-34° C. The dialysis machine may be operable to reduce the temperature of the treatment fluid already during CPR or when a cardiac rhythm has been restored in the patient following CPR/defibrillation.

It has been previously suggested to cool dialysis patients by lowering the temperature of the treatment fluid, e.g. to 35-36° C., for the purpose of improving the cardiovascular tolerance to hemodialysis treatment, in particular to reduce the risk for hypotension in dialysis patients during hemodialysis. Reference is given to the article "Thermal balance and dialysis hypotension" by Q Maggiore et al, published in *Int J Artif Organs*, 18:518-525 (1995), and in the article "Blood temperature and vascular stability during hemodialysis and hemofiltration" by Q Maggiore et al, published in *Trans Am Soc Artif Intern Organs*, 28:523-527 (1982).

As a further feature, in all embodiments disclosed herein, the dialysis machine may be configured to change the composition of the blood pumped to the patient upon generation of the CA alarm signal, for the purpose of restoring a cardiac rhythm and facilitating the recovery of the patient. The composition may be changed indirectly, by changing the composition of the treatment fluid in the TF circuit 1*b*, or directly, by manipulating the blood in the EC circuit 1*a*. The dialysis machine may be operable to change the blood composition either automatically or on command, and the dialysis machine may allow the rescue staff to enter or select a desired composition change via a user interface on the dialysis machine. It is also possible for the rescue staff to manually administer drugs and substances via one or more existing administration ports on the blood line set connected to the dialysis machine.

It is known procedure to administer drugs and other substances to a cardiac arrest patient before, during and after CPR and defibrillation, e.g. as disclosed by the American Heart Association, in Circulation. 2005; 112; IV-58-IV-66: "*Part 7.2: Management of Cardiac Arrest*". Normally, the rescue staff needs to establish an intravenous (IV) access and then consider drug therapy. By using the dialysis machine for supplying relevant drugs and substances, an additional establishment of an IV access is not needed and drug therapy may directly be commenced or considered.

With respect to drug therapy, the above-identified article by the American Heart Association suggests the use of many different drugs, including vasopressors, epinephrine, vasopressin, atropine, amiodarone and lidocaine. The dialysis machine may be equipped with a dedicated set of such drugs to be administered by the dialysis machine to the patient in the event of a CA alarm.

It is also known or believed to be useful to administer any one of saline solution, calcium chloride (CaCl), sodium chloride (NaCl), calcium gluconate, citrate, heparin, potassium and magnesium. Many of these substances are used by the dialysis machine in its normal operation. Thus, it may be possible for the dialysis machine to create a proper composition of the blood without having access to dedicated substances for cardiac arrest treatment. The dialysis machine may be further configured to increase the efficiency by which the drugs or substances are administered to the patient by changing its machine settings, e.g. one or more of treatment fluid flow rate, blood flow rate and ultrafiltration rate. It has also been reported that it may be beneficial to administer glucose to a patient suffering from cardiac arrest. At least in certain clinical settings, standard dialysis machines have access to glucose, which may be mixed into the treatment fluid at an adequate concentration.

Another known procedure in connection with cardiac arrest is to insert an airway adjunct to provide ventilation and oxygenation of the patient before, during and after CPR and defibrillation. According to one aspect, the dialysis machine is configured to change the composition of the blood so as to establish similar effects as an artificial lung, thereby reducing or eliminating the need to insert an airway adjunct while the patient is connected to the dialysis machine. For example, the dialysis machine may change the amount of bicarbonate in the treatment fluid. The amount of bicarbonate affects the amount of CO2 in the patient, which influences the patient's ability to breathe. Furthermore, bicarbonate affects the pH of the patient, and keeping a normal pH in the body has been reported to be beneficial for cardiac arrest patients. In some clinical settings, the dialysis machine is connected to an $O_2/CO_2$ gas exchanger which sets the amount of oxygen and carbon dioxide in the blood pumped through the EC circuit 1*a*. By controlling the gas exchanger, the dialysis machine may act as an artificial lung by controlling both the amount of oxygen given to the patient and the amount of carbon dioxide removed from the patient.

Embodiments of the invention relate to methods and structures in the monitoring device 7 for enabling fast, sensitive and specific detection of a CA incident in the patient. One specific challenge in designing the monitoring device 7 is to reduce the risk for false positives (false alarms) without increasing the risk for false negatives (missed CA incidents). The method and structure that are described in detail below implement three different concepts that each improve the CA monitoring technique in this respect.

Figure 2A:
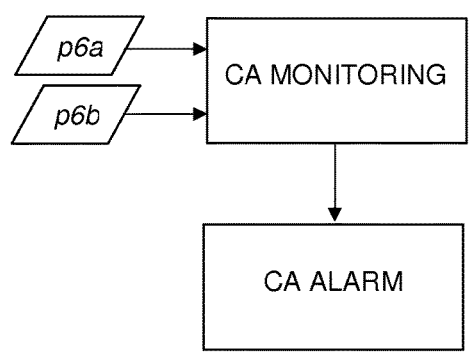
FIGS. 2A-2C are examples of first, second and third concepts for improving an inventive technique for monitoring of cardiac arrest.

A first concept is to use more than one pressure signal in the CA monitoring, such that a CA alarm is only generated if an absence of heart pulses is detected in two or more pressure signals. The first concept is schematically exemplified in FIG. 2A, where the CA monitoring processes the venous and arterial pressure signals p6a, p6b for detection of absence of heart pulses. The first concept will improve the specificity of the monitoring technique, since it becomes less sensitive to other fault conditions in the EC circuit 1a and its connection to the patient. The first concept also improves the accuracy by reducing the risk for false positives without increasing the risk for false negatives.

Figure 2B:
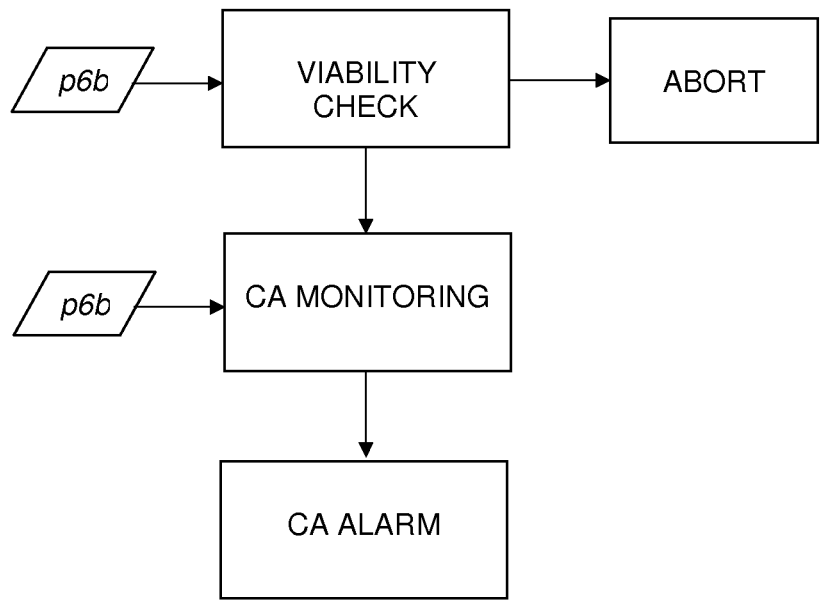

A second concept is to perform an initial viability check or viability evaluation before the CA monitoring is initiated. The viability check aims at ensuring that heart pulses are detectable in the pressure signal(s) that are to be used in the subsequent CA monitoring, and this is achieved by applying enabling criteria for CA monitoring. The second concept is schematically exemplified in FIG. 2B, where a viability check is performed to evaluate if the arterial pressure signal p6b is useful for CA monitoring. If the signal p6b passes the viability check, the CA monitoring is initiated, otherwise the process is aborted. The viability check may also be implemented to actively select the pressure signal(s) to be used in the CA monitoring as well as set the test or tests that are to be used for detecting or verifying presence/absence of heart pulses in the respective pressure signal during the CA monitoring. The second concept serves to reduce the risk for false positives without increasing the risk for false negatives. The second concept also allows the CA monitoring to be automatically adapted and optimized to a specific treatment session. It should be realized that the magnitude of the heart pulses in the pressure signals may differ considerably between different patients, and between treatment sessions for the same patient, e.g. depending of the positioning of the access devices 2', 2" in the vascular access 3.

Figure 3C:
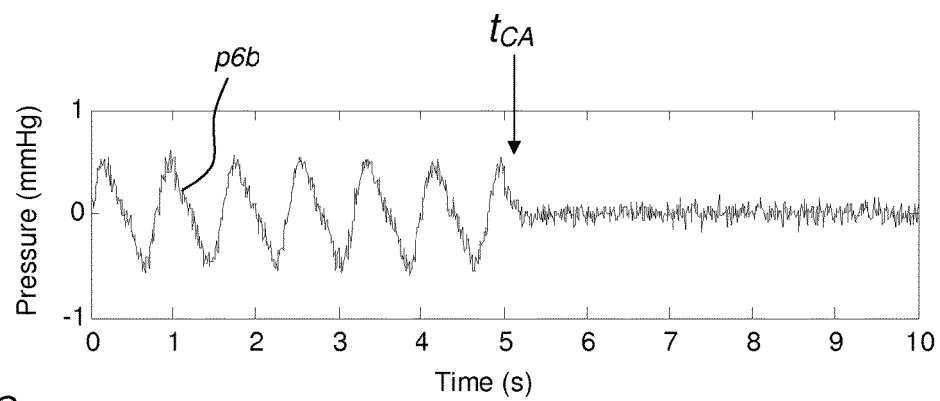
Figure 4C:
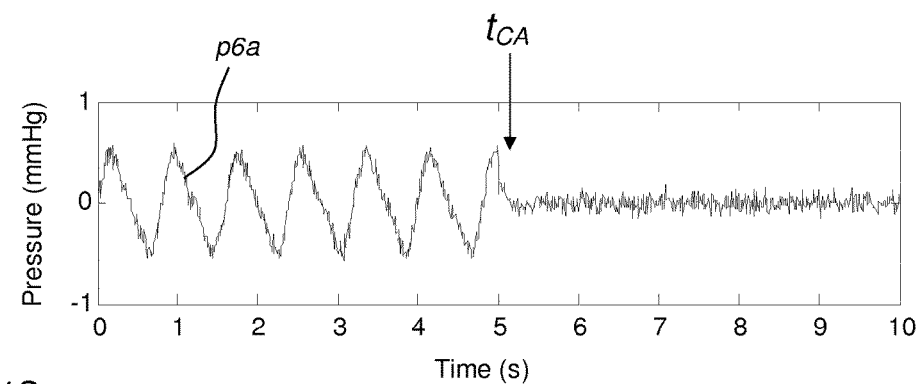

A third concept is to separate the CA monitoring into a detection phase and a verification phase, where the detection phase is carried out while the blood pump is active (i.e. during on-going blood treatment) and aims at detecting a possible CA incident. If a possible CA incident is detected, the CA monitoring operates to stop the blood pump (and possibly other sources of disturbances) and switches to the verification phase to verify if the heart pulses have indeed disappeared in the pressure signal(s). Thus, during the verification phase, the pressure signals are essentially free of disturbances, which will improve the accuracy of the parameter values that are computed to represent the presence or absence of the heart pulses in the pressure signal(s). This is further illustrated in FIGS. 3C and 4C, which shows the arterial and venous pressure signals p6b, p6a when the blood pump 4 has been stopped. Compared to FIGS. 3B and 4B, the disappearance of the heart pulses at time $t_{CA}$ is even more evident. It may be noted that the filtering may be modified or even completely disabled during the verification phase, to ensure that the heart pulses are not distorted or accidentally eliminated. For example, any filtering that is tailored to remove or suppress pump pulses may be disabled during the verification phase. It is realized that the third concept serves to reduce the risk for false positives without increasing the risk for false negatives.

Figure 2C:
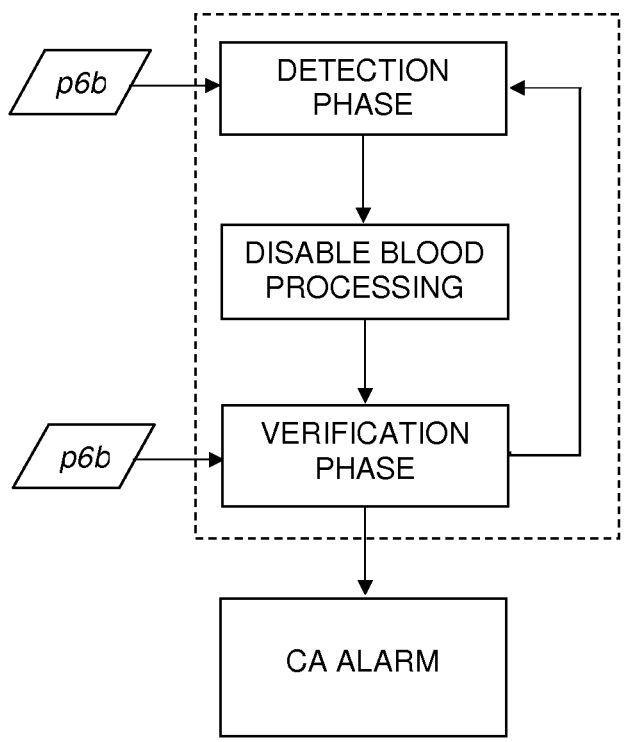

The third concept is schematically exemplified in FIG. 2C, in which the CA monitoring (dashed box) operates on the arterial pressure signal p6b. If an absence of heart pulses is detected in the detection phase during ongoing blood treatment, the blood treatment is stopped to suppress disturbances in the pressure signal p6b and the verification phase is initiated to investigate if the heart pulses indeed are absent in the pressure signal p6b. If the verification phase determines that the heart pulses are absent, the CA alarm is generated, otherwise the CA monitoring may return to the detection phase.

Depending on implementation, the monitoring device 7 may use digital components or analog components, or a combination thereof, for receiving and processing signals. For example, the device 7 may be a computer, or a similar data processing device, with adequate hardware for acquiring and processing signals in accordance with different embodiments of the invention. Embodiments of the invention may be implemented by software instructions that are supplied on a computer-readable medium for execution by a processor PROC in conjunction with an electronic memory MEM in the device 7, as indicated in FIG. 1.

Figure 5:
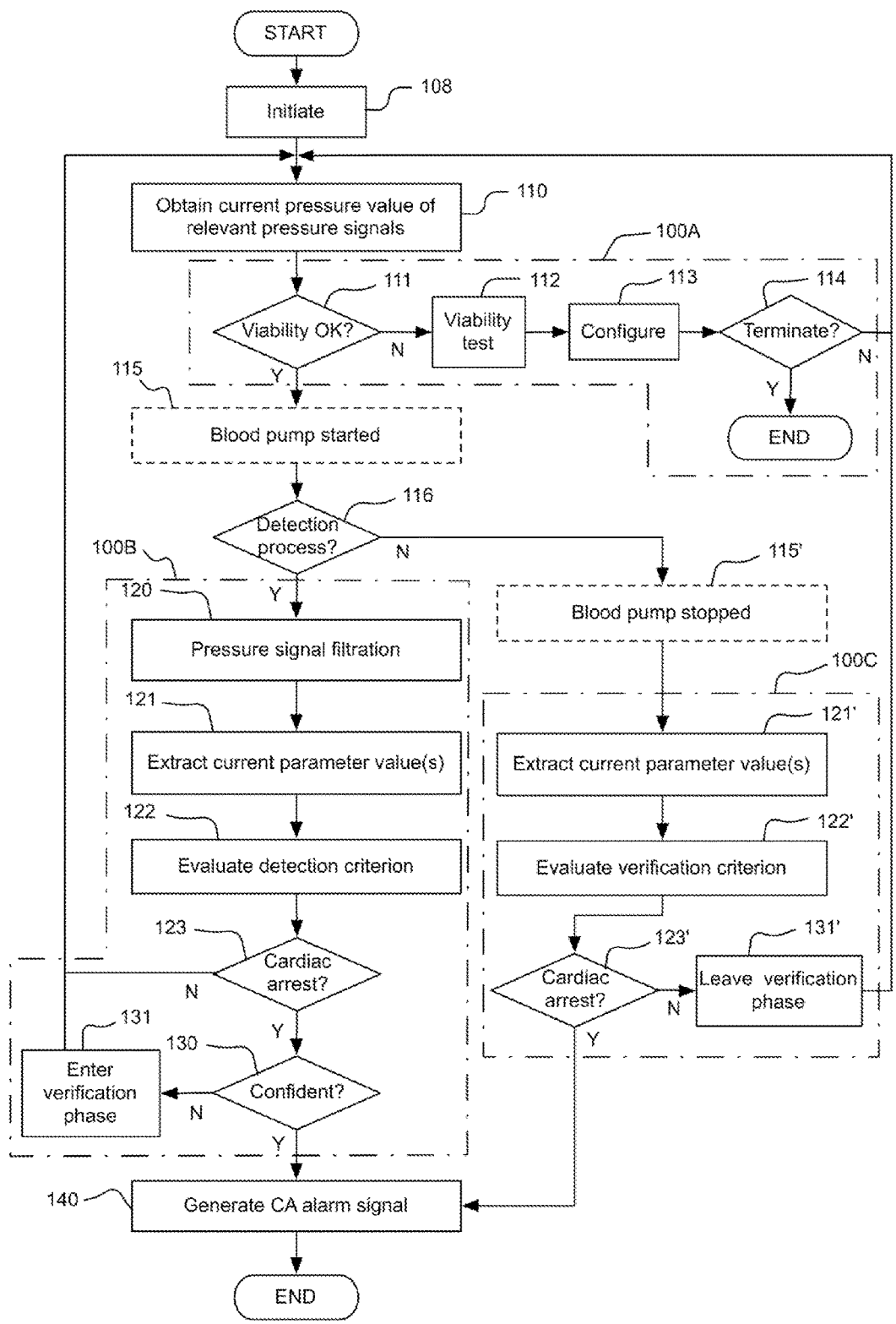
FIG. 5 is a flowchart of an exemplifying method of monitoring cardiac arrest in the apparatus in FIG. 1.

FIG. 5 is a flow chart intended to represent the principal operation of a specific method for CA monitoring which implements all of the above-mentioned concepts. Thus, the method in FIG. 5 is operable in a viability checking phase, a detection phase, and a verification phase, by executing steps indicated by dashed box 100A, 100B, and 100C, respectively. The flow chart is merely provided to facilitate the following discussion and it does not present all details of the operation. The method operates, by step 110, to repeatedly acquire a current pressure value from one or more pressure signals, and the method may follow different flow paths and execute different sub-processes during the different repetitions. For the sake of simplicity, control parameters used for causing the method to switch between these different flow paths are omitted in FIG. 5 and not discussed in further detail. It lies within the reach of the person skilled in the art of electronics design and computer programming to implement such control parameters. To further facilitate the understanding of the method, FIGS. 6A-6J are provided to illustrate the flow paths in FIG. 5 that correspond to different sub-processes.

Even if the method in FIG. 5 is illustrated to repeatedly obtain and process a current data sample (pressure value) from the respective pressure signal, in step 110, it is to be understood that subsequent steps of each repetition need not (but may) operate only on the current data sample but rather operate on a collection of recent data samples, e.g. within a time window of the pressure signal. For example, the evaluation parameter(s) that are used in the CA monitoring (see steps 121-122 and 121'-122' below) may be computed within a predefined parameter computation window in the respective pressure signal. The length of the parameter computation window may be set differently for different evaluation parameters.

Furthermore, even if the method is illustrated to operate on discrete data samples, i.e. digital data, it lies within the reach of the skilled person to modify the method to operate on analog data. When the method operates on digital data, step 110 may produce data samples at a fixed or a variable rate.

Generally, it should be noted that the branching steps in the flow chart, e.g. steps 111, 123, 123' and 130 as described below, require the respective test to be passed for a given time segment in the respective pressure signal. Thus, the viability checking phase will not be deemed to be completed until the viability test in step 112 has been passed for a given time segment in the respective pressure signal. Similarly, the method will continue in the detection phase until a given CA test (or plural CA tests) in step 122 has been passed for a given time segment in the respective pressure signal. Likewise, the method will only generate the CA alarm signal in the verification phase when the CA test (or tests) in step 122' has been passed for a given time segment in the respective pressure signal. The length of the time segment may differ between the different branching steps 111, 123, 123' and 130. In steps 122, 122', the time segment defines a "CA test period", which is suitably set to exceed the time difference between heart pulses. Generally, the CA test period may be set to contain in the range of 1-100 heart pulses, and typically at least 5 heart pulses. The CA test period may be a predefined time interval, which may be set based on the expected maximum time interval between heart pulses, which may have been determined for the specific patient that is being treated or for a general population of patients. To achieve a consistent accuracy for the CA monitoring, the CA test period may instead be adapted dynamically, based on the current heart rate of the patient, so as to include a predefined number of heart pulses. The number of heart pulses within the CA test period generally affects how accurately a disappearance of heart pulses is detected in a given pressure signal.

It should be noted that steps 122, 122' may require that the respective CA test is passed at least a given number of times, or at a given percentage, during the CA test period. In the following, this is referred to as the required "pass rate" of the detection phase and the verification phase, respectively.

In the embodiment of FIG. 5, the pressure values from different pressure signals are acquired and processed essentially concurrently, to enable a short response time and accurate detection. However, in variants, pressure values from different pressure signals may be acquired and processed with a mutual time delay during one or more of the viability checking phase, the detection phase and the verification phase. For example, the different pressure signals may be tested sequentially during the CA tests(s) for disappearance of heart pulses.

Figure 6A:
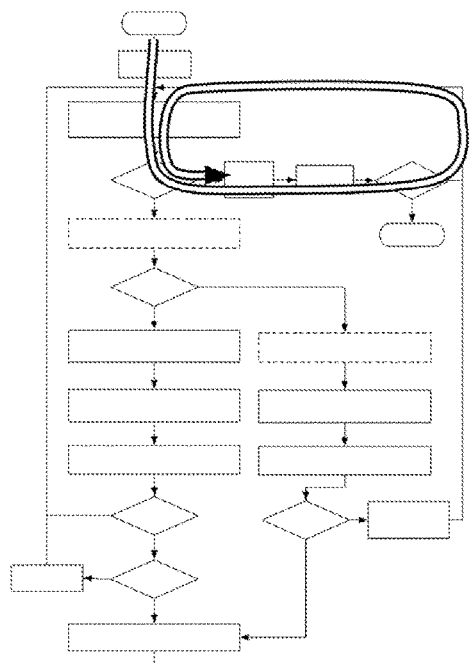
FIGS. 6A-6J illustrate different sub-processes within the method in FIG. 5.
Figure 6B:
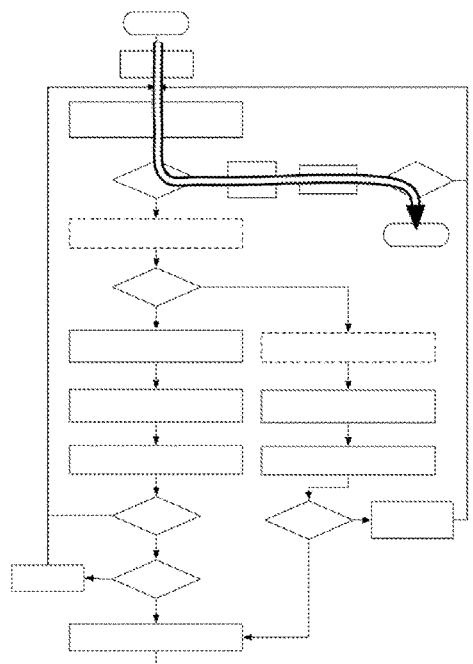

The method in FIG. 5 starts by performing an initiation step 108 in which various control parameters of the method are initiated. Step 108 may also set default values (settings) for the CA monitoring, such as the tests and associated thresholds to be applied in the viability checking phase 100A, the detection phase 100B, and the verification phase 100C, respectively, the length of the parameter computation window, the length of the CA test period, the required pass rates of the detection and verification phases, etc. The method then enters the viability checking phase 100A, by repeatedly executing steps 110, 111, 112, 113 and 114, as indicated in FIG. 6A. The method stays in the viability checking phase 100A until either step 112 signals that the viability checking phase 100A is successfully completed, or step 112 signals that the CA monitoring cannot be performed with adequate accuracy. In the latter case, step 114 terminates the method, as indicated in FIG. 6B. Step 112 executes a viability test which may e.g. involve identifying individual heart pulses in the available pressure signals p6a-p6c from the pressure sensors 6a-6c in the blood treatment apparatus and assessing if the magnitude of the heart pulses in each of these pressure signals p6a-p6c is large enough to be used for CA monitoring, e.g. by comparing the magnitude to a viability threshold, which may or may not be specific for each pressure signal. For example, the viability threshold may be indicative of an actual or expected magnitude of the above-mentioned residuals in the respective pressure signal during the subsequent detection phase, i.e. the interfering signal components that remain in the pressure signal after filtering when the blood pump is running. In one implementation, the magnitude of these residuals have been measured for different pumping rates of the blood pump 4 and stored in a database in electronic memory (MEM in FIG. 1), whereby the initiation step 108 accesses the database at startup and selects the viability threshold to be used in step 112 based on the blood pumping rate to be used during the blood treatment, assuming that the blood pumping rate has already been selected and entered by the operator of the blood treatment apparatus. In another implementation, the viability checking phase executes a preparatory measurement process (not shown), in which pressure values are acquired (step 110) from the respective pressure sensor and filtered for pump pulse suppression (cf. step 120), while the magnitude of the residuals is measured in the respective pressure signal and used for setting the viability threshold. In an alternative, which is equivalent to the foregoing implementations, step 112 may normalize the magnitude of the heart pulses by the actual or expected magnitude of residuals, so as to generate an actual or expected SNR (signal-to-noise ratio) which step 112 then compares to a predefined SNR threshold.

If a predetermined number of pressure signals p6a-p6c pass the viability test, step 112 may indicate for step 111 that the viability checking phase 100A is successfully completed, otherwise step 112 may indicate for step 114 that the method is to be aborted. Generally, the predetermined number may be 1. However, since the illustrated method implements the above-mentioned first concept, the predetermined number is at least 2. In the forthcoming repetitions, the method proceeds to step 115 from step 111. It should be noted that, in these repetitions, step 110 operates to obtain data samples only from the pressure signals that have passed the viability test, these pressure signals being denoted "supervised signals" in the following.

In an alternative, step 112 only indicates that the viability checking phase 100A is successfully completed if and when one or more mandatory pressure signals pass the viability test. For example, step 112 may require that one mandatory pressure signal and one further pressure signal passes the test. For example, the arterial signal p6b and/or the venous signal p6a may be mandatory while the TF signal p6c is optional.

In the illustrated embodiment, the viability checking phase 100A also involves a configuration step 113 which sets the criterion to be used for detecting a CA incident in the detection phase and/or the verification phase (cf. steps 122 and 122' below). In one example, step 113 sets a respective operative threshold for each supervised signal based on the magnitude of the heart pulses in this signal (and optionally based on the actual or expected magnitude of the residuals). The operative threshold may e.g. be set to a given fraction of the magnitude of the heart pulses, provided that the operative threshold still exceeds a predefined minimum detection level for the respective supervised signal. The operative threshold may also be set with a given margin to the actual or expected magnitude of the residuals. It should be noted that different operative thresholds may be set for the detection phase and the verification phase. In another example, step 113 sets the required pass rate to be applied in step 122. In yet another example, step 113 selects one or more CA tests among a plurality of available CA tests (see below), based on the magnitude or rate of the heart pulses in the respective pressure signal.

The configuration step 113 may also be implemented to dynamically determine the above-mentioned minimum detection level for the respective supervised signal. The minimum detection level may be determined based on the noise characteristics (e.g. standard deviation or RMS) in the respective pressure signal, to indicate the smallest magnitude of heart pulses that can be reliably detected in the respective supervised signal. The noise characteristics of the respective pressure signal are preferably analyzed before the circuit 1a is connected to the subject and while the apparatus for blood treatment is non-active, such that the respective pressure signal is free of heart pulses from the patient and signal disturbances from the blood pump 4 and other sources of disturbances in the apparatus for blood treatment.

The configuration step 113 may, alternatively or additionally, be implemented to actively select the predetermined number of pressure signals (i.e. the supervised signals) among the available pressure signals, based on the magnitude of the heart pulses in the respective pressure signal, e.g. such that the subsequent CA monitoring is tailored to operate on the pressure signals with the strongest heart pulses. The configuration step 113 may apply further constraints on the pressure signals to be selected as supervised signal, e.g. that the apparent rate of the heart pulses is identical in the pressure signals (cf. CA test II below) and/or that the shape of the respective pressure signal agrees with presence of heart pulses (cf. CA test VII below). Thus, even if a pressure signal seems to contain strong heart pulses, it may be discarded if it yields a deviating rate of heart pulses and/or has a shape that would not occur if only heart pulses were present in the pressure signal.

In the illustrated example, the blood pump 4 is stopped during the viability checking phase 100A, possibly together with all other controllable sources of disturbances in the EC circuit 1a and the TF circuit 1b, such that the viability checking phase 100A is performed essentially without any disturbances in the pressure signals. This may improve the accuracy of the estimated magnitude of the heart pulses in the respective pressure signal. This may, in turn, improve the accuracy of the operative thresholds if step 113 is implemented to set these based on the magnitude of the heart pulses. As indicated by step 115, the blood pump 4 is started (or allowed to be started by another process in the apparatus for blood treatment) when step 111 detects that the viability checking phase 100A has been successfully completed. The blood pump 4 then remains active during the subsequent repetitions of the method, unless intermittently stopped in step 115', see below.

In a variant, the blood pump 4 is active during the viability checking phase 100A, and the pressure signals are filtered for suppression of disturbances, e.g. using any of the known filtering techniques discussed above in relation to FIG. 1. This variant may improve the ability of step 112 to determine if the magnitude of the heart pulses are sufficient to be detected in the detection phase, i.e. in presence of the above-mentioned residuals. One potential drawback of this variant is that it may be difficult to distinguish between heart pulses and residuals during the viability checking phase 100A. This potential problem may be overcome by having the blood pump 4 disabled during one part of the viability checking phase and active during another part of the viability checking phase (in which the pressure signals are filtered for suppression of disturbances), e.g. to improve the ability of step 112 to determine if the magnitude of the heart pulses are sufficient to be detected in verification phase and the detection phase, respectively. Step 112 may consider a pressure signal to pass the viability test only if the heart pulses are deemed to be detectable in both the verification phase and the detection phase.

Figure 6C:
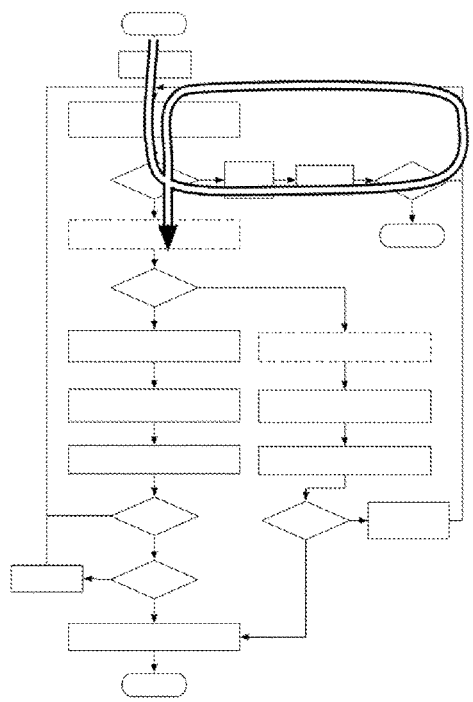
Figure 6D:
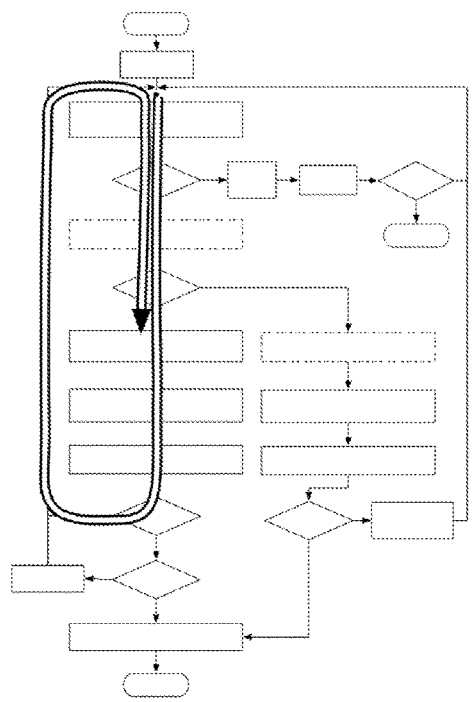

When the viability checking phase is completed, the method causes the blood pump 4 to be started (step 115), if not already started, and enters the detection phase 100B. This transition is indicated in FIG. 6C. In the detection phase 100B, the method is directed by step 116 to repeatedly execute steps 110, 120, 121, 122 and 123, as indicated in FIG. 6D. The method stays in the detection phase 100B until step 122 signals to step 123 that a potential CA incident has occurred. Step 120 generates a current filtered pressure value for each supervised signal, and step 121 operates on the filtered pressure value (and most likely preceding filtered pressure values for the respective supervised signal) to extract a current value of an evaluation parameter, which may be a magnitude, a heart rate, a correlation value or a statistical shape measure, as will be discussed further below. Depending on implementation, step 121 may not produce an evaluation parameter value for each repetition of the method. If no evaluation parameter value is produced in step 121, the method may proceed directly to step 110 for a new repetition in the detection phase 100B. Otherwise, the method proceeds to step 122, which applies a detection criterion to detect a disappearance of the heart pulses in the supervised signals. The detection criterion involves one or more CA tests and indicates a potential CA incident, if fulfilled. If step 122 is affirmative, step 123 directs the method to step 130, otherwise the method proceeds to step 110 for a new repetition in the detection phase 100B.

Figure 6E:
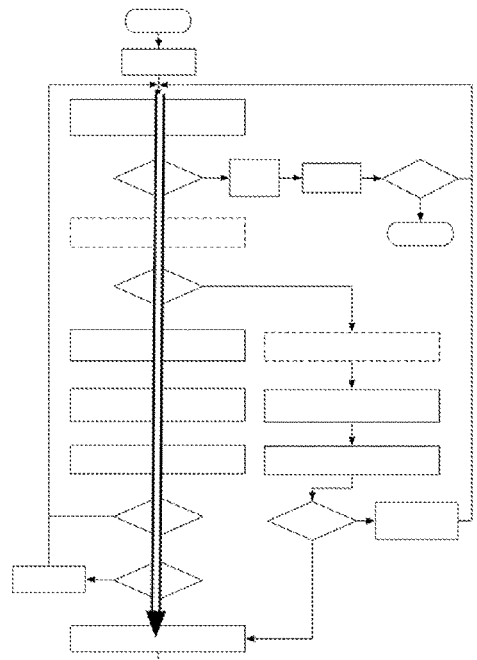
Figure 6F:
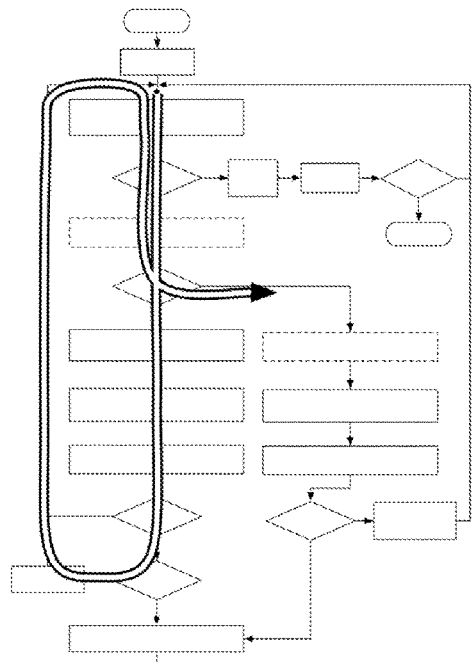

Step 130 is implemented to evaluate the confidence level of the potential CA incident. If the confidence level is sufficient, step 130 directs the method to step 140 which generates the CA alarm signal, as indicated in FIG. 6E, otherwise the method proceeds to step 131, which initiates the verification phase. This transition is indicated in FIG. 6F. In one implementation, the confidence level may be determined in step 130 based on the number of supervised signals that indicate the potential CA incident in step 122. For example, the confidence level may be deemed sufficient if at least two or at least three supervised signals indicate the potential CA incident. If the detection phase 100B operates on a subset of all available pressure signals, it is conceivable that step 130 performs a separate test to verify that there are no detectable heart pulses in any of the other pressure signals before directing the method to step 140.

In another implementation, the confidence level may be determined in step 130 by the number of "CA tests" that indicate the potential CA incident for the respective supervised signal in step 122. For example, step 122 may apply different CA tests and/or apply two or more operative thresholds for a specific CA test to assess if the heart pulses have disappeared in the respective supervised signal. The operative thresholds may be set to yield different reliability in the detection of a potential CA incident. For example, when the evaluation parameter represents the magnitude of the heart pulses, an increased reliability may be obtained with decreasing threshold. In another example, step 122 may apply different CA test periods to assess if the heart pulses have disappeared, where an increased reliability may be obtained with a longer CA test period.

In another implementation, the confidence level may be determined in step 130 based on the actual pass rate of the respective CA test in step 122.

In a further implementation, the confidence level may be deemed sufficient by step 130 if a potential CA incident identified by step 122 is corroborated by a secondary indication. One such secondary indication is that the static pressure at the arterial sensor 6*b* (FIG. 1) has not increased or decreased significantly and rapidly during a proceeding time period (e.g. 5-10 seconds). The meaning "static pressure" is well-known to the person skilled in the art and refers to the baseline pressure level on which the heart pulses (and disturbances) are superimposed in the arterial signal p6*b*. The static pressure at the arterial sensor 6*b* is dominated by the pressure drop in the arterial access device 2' when blood is pumped through it, and this pressure drop will decrease significantly (or essentially disappear) if the arterial access device 2' has been dislodged from the vascular access 3 and is taking in air instead. Alternatively, if the arterial access device 2' is dislodged and is blocked, e.g. by a piece of clothing or the bed sheets, the static pressure at the arterial pressure sensor 6*b* will decrease abruptly. Thus, if the supervised signals include the arterial signal p6*b*, the use of this secondary indication in step 130 may prevent a dislodgement of the arterial access device 2' to result in generation of the CA alarm signal. It should be noted it will also prevent the CA alarm signal from being generated if both access devices 2', 2" are dislodged from the access 3. Another secondary indication may be that an existing air detector (not shown) in the EC circuit 1*a* does not signal that air has been detected in the blood flow. If the secondary indication is not fulfilled, step 130 may initiate generation of an "arterial dislodgement alarm signal" to alert the staff to check the connection of the EC circuit 1*a* to the patient.

It is to be understood that the confidence level may be determined by any combination of the above-described methodologies.

In an alternative, step 130 is omitted and instead step 123, if step 122 is affirmative, directs the method to step 131 which initiates the verification phase.

Figure 6G:
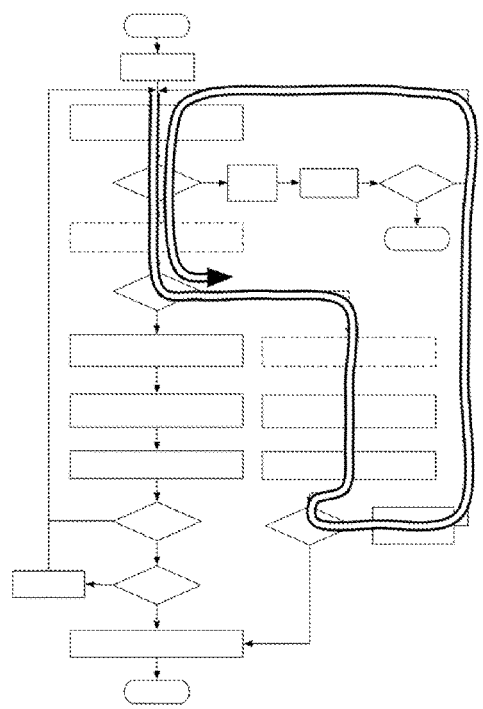

When the detection phase 100B is completed, the method is directed by step 116 to stop the blood pump 4 and possibly other sources of disturbances in the apparatus for blood treatment (step 115'), and enters the verification phase 100C. The source(s) of disturbances then remain stopped during subsequent repetitions (if any) of the method in the verification phase. In the verification phase 100C, the method repeatedly executes steps 121', 122', 123' and 131', as indicated in FIG. 6G. Step 121' corresponds to step 121, but operates on the non-filtered pressure value obtained in step 110 to extract a current value of an evaluation parameter, which may be a magnitude, a heart rate, a correlation value or a statistical shape measure, as will be discussed further below. In an alternative (not shown), step 121' instead operates on a filtered pressure value, which may be obtained from a step similar or identical to step 120. As in step 121, step 121' need not produce an evaluation parameter value for each repetition of the method. If no evaluation parameter value is produced in step 121', the method may proceed directly to step 110 for a new repetition in the verification phase 100C. Otherwise, the method proceeds to step 122', which applies a verification criterion to detect if the heart pulses really have disappeared in the supervised signals. The verification criterion involves one or more CA tests and indicates a confirmed CA incident, if fulfilled. The CA tests used in step 122' may be identical to the CA tests used in step 122, although it is possible that stricter (lower) thresholds are used in step 122' compared to step 122. Alternatively, step 122' may apply a CA test which is not applied in step 122, and vice versa. Even if the detection and verification phases 100B, 100C operate on a subset of all available pressure signals, it is conceivable that the verification phase 100C operates on all available pressure signals to verify that there are no detectable heart pulses in any of the available pressure signals.

Figure 6H:
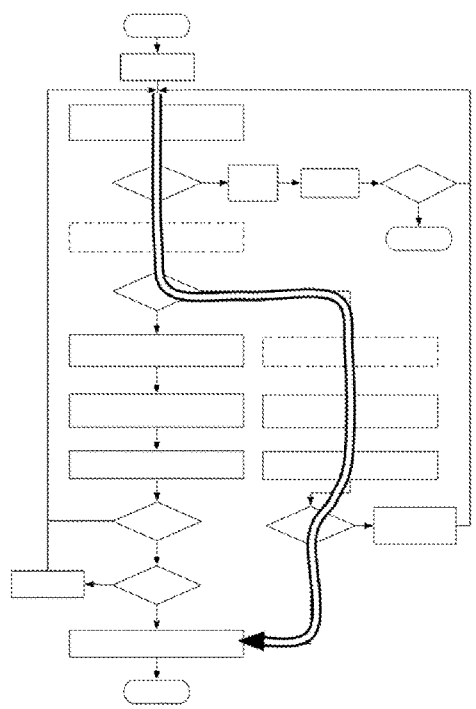
Figure 6I:
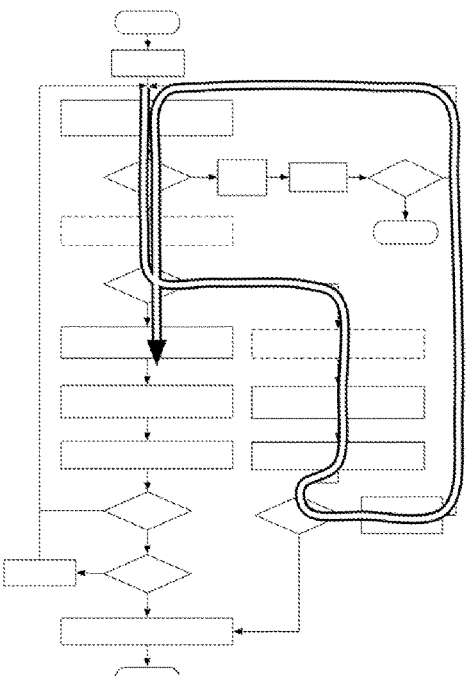

If step 122' is affirmative, step 123' directs the method to step 140, as indicated in FIG. 6H, otherwise the method proceeds in the verification phase 100C until step 131' signals that the method should leave the verification phase 100C. Step 131' is thus configured to interrupt the verification phase 100C, e.g. when the method has operated for a given time-out period in the verification phase 100C without step 122' indicating a confirmed CA incident. Step 131' may be implemented to direct the method to start the blood pump in step 115 and re-enter the detection phase 100B, as indicated in FIG. 6I.

Figure 6J:
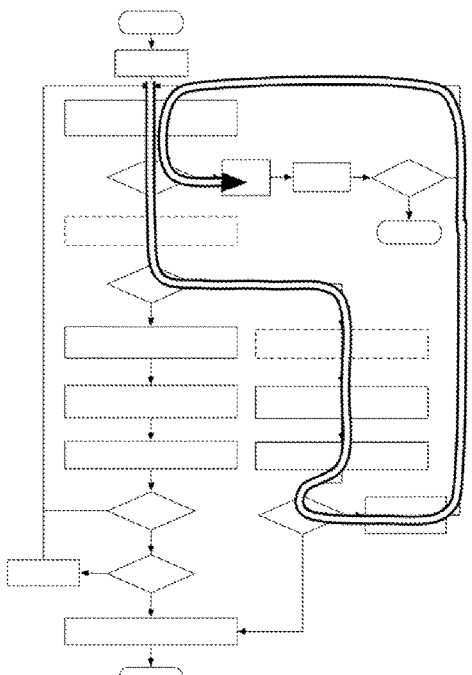

In a variant, step 131' may be implemented to direct the method to the viability checking phase 100A, as indicated in FIG. 6J. It may be undesirable that the method switches back and forth between the detection and verification phases 100B, 100C, causing the blood pump 4 to be switched on and off, and this may be avoided by instead directing the method from the verification phase 100C to the viability checking phase 100A, in which steps 112-113 may test the pressure signals and possibly modify the selection of pressure signals or the criterion to be used for detecting a CA incident in the detection phase 100B and/or the verification phase 100C. It is conceivable that step 131' directs the method to re-enter the detection phase 100B by default, and to direct the method into the viability checking phase 100A after a given number of successive transitions from the detection phase 100B to verification phase 100C.

Although not shown in FIG. 5, the method may also include a further configuration step that actively modifies the method based on the current operating parameters of the apparatus for blood treatment. One such operating parameter is the blood flow rate (pumping rate of blood pump 4), which may affect the amount of residuals in the filtered pump signal. The method may, e.g., be modified by changing the selection of supervised signals or the criterion to be used for detecting a CA incident in the detection phase 100B based on the current operating parameters of the apparatus for blood treatment. In one example, different CA tests or combinations of CA tests (see below) may be used for different values of the operating parameters of the apparatus for blood treatment. In another example, a threshold value used in one or more CA tests may be modified based on the current operating parameters, e.g. to account for the expected magnitude of residuals in the filtered pressure signal(s) for a given blood pumping rate. The expected magnitude of residuals may be derived from a database of the electronic memory, as discussed above in relation to step 112.

In a variant, the further configuration step may actively modify the current operating parameters of the apparatus for blood treatment to improve the CA monitoring. As noted above, it may be difficult to properly filter the pressure signals when the heart rate overlaps a frequency component of the blood pump. To avoid such overlap, the further configuration step may detect if the heart rate (e.g. determined in step 121) approaches or overlaps a frequency component of the blood pump 4 and actively control the pumping rate of the blood pump 4 to separate the heart rate from the frequency components of the blood pump. This presumes that the pumping rate is known, which may be achieved as described below in relation to CA test IV. It is also conceivable that the further configuration step actively steers the blood pump 4 away from the pumping rates that are known to yield relatively large residuals in the filtered pressure signal (e.g. based on the above-mentioned database stored in electronic memory).

Steps 122 and 122' may apply one or more of the following CA tests.

I) If the evaluation parameter represents the estimated magnitude of heart pulses, the CA test may be fulfilled if the estimated magnitude for a predetermined number of the supervised signals is less than a magnitude threshold.

II) If the evaluation parameter represents the estimated heart rate, the CA test may be fulfilled if the estimated heart rate differs between a predetermined number of the supervised signals. If the heart pulses disappear in the supervised signals, step 121, 121' is likely to identify another frequency component in the respective supervised signal as the heart rate, and the identified frequency component is not unlikely to differ between the supervised signals. This is especially true during the verification phase 100C, since the blood pump 4 is disabled and the supervised signals are free of frequency components that originate from the blood pump. However, CA test II may also be applied by step 121 during the detection phase 100B.

III) If the evaluation parameter represents the estimated heart rate, the CA test may be fulfilled if the estimated heart rate is outside a predefined range for a predetermined number of supervised signals. The predefined range may be defined by physiological limits for a general population of patients, or for the specific patient that is connected to the apparatus for blood treatment. In one example, the predefined range may be 50-180 bpm (beats per minute). In another example, the lower limit of the predefined range is zero, which means that the CA test is fulfilled if the estimated heart rate is close to zero. As explained in the Background section, detecting a heartbeat that is close to zero may be difficult and requires that the heart rate estimation in step 121, 121' is implemented with special attention to prevent that any other frequency component in the respective supervised signal is identified as the heart rate when the heart pulses disappear.

IV) If the evaluation parameter represents the estimated heart rate, the CA test may be fulfilled if the estimated heart rate becomes equal to a frequency component of the pump (either the base frequency or one of its harmonics) for a predetermined number of the supervised signals. It is realized that CA test IV is only applicable to the detection phase 100B, i.e. in step 122, when the blood pump is running. If the heart pulses disappear, the supervised signals may be dominated by the residuals from the pump and step 122 may identify a frequency of the pump as the heart rate. This CA test presumes that the pumping rate is known. The pumping rate may be obtained from a reference signal REF, which is generated by a reference sensor (not shown) to indicate the current operating frequency of the blood pump 4. In one example, the reference sensor is a tachometer associated with the blood pump to measure the rotation speed of an element (e.g. a rotor) in the power transmission of the blood pump. Such a tachometer may be configured to provide any number of readings representative of the rotation speed during each rotor revolution, e.g. at a single instance or at plural instances during each rotor revolution. In another example, the reference signal REF is a control signal for the blood pump 4, e.g. indicating a set value for the blood flow rate or the pumping rate of the pump, or indicating the current/power fed to a motor that drives the pump. Alternatively, the pumping rate may be estimated by processing one or more of the pressure signals, preferably before the pressure signals are processed in the filtering step 120. There are many techniques, well known to the skilled person, for determining the current operating frequency of the blood pump 4 from either the reference signal or the non-filtered pressure signal.

V) If the evaluation parameter represents the estimated heart rate, the CA test may be fulfilled if the estimated heart rate exhibits a rapid temporal change, e.g. a step change, for a predetermined number of the supervised signals. Such a rapid change may occur if the heart pulses suddenly disappear. It may also occur if pressure variations from another signal source happens to dominate over the heart pulses in the supervised signal(s), e.g. if the patient suffers from a seizure. Thus, CA test V is primarily suited for use in the detection phase 100B, i.e. in step 122, and may be used to trigger the method to enter the verification phase 100C.

In CA tests I, III, IV and V, the "predetermined number" may be 1, but is preferably at least 2 or at least 3. In test II, the "predetermined number" may be at least 2 or at least 3.

VI) If the evaluation parameter represents a correlation between a predetermined number of pairs of supervised signals, the CA test may be fulfilled if the correlation is less than a correlation threshold. It is realized that if the heart pulses disappear in one or both of the supervised signals, the correlation between the supervised signals is likely to decrease. In CA test VI, the "predetermined number" may be at least 1 or at least 2. The correlation may be represented by a "correlation value", which may be computed by taking the scalar product between time segments of pressure values in the supervised signals. The correlation value may (but need not) be normalized, e.g. by the standard deviation of the pressure values in the respective time segment (to yield a correlation coefficient).

VII) If the evaluation parameter is a statistical measure that represents the shape of the respective supervised signal, the CA test may be fulfilled if the statistical measure indicates a sufficiently sinusoidal distribution of pressure values in a predetermined number of supervised signals. This may be determined by comparing the statistical measure to a statistics threshold. The "predetermined number" may be 1, but is preferably at least 2 or at least 3. CA test VII is based on the insight that the sequence of heart pulses in the supervised signal resembles a sinusoid, and that the disappearance of the heart pulses may result in a less sinusoidal shape of the supervised signal. The statistical measure may be a so-called standardized moment of third order or higher, which is computed for a time segment of pressure values in the supervised signal. This type of statistical measure offers a computationally efficient way of analyzing the shape of the respective supervised signal. The standardized moment of third order, also known as "skewness", is defined as the third central moment of a set of data samples, divided by the cube of the standard deviation of the set of data samples. Skewness is a measure of asymmetry around a sample mean. The standardized moment of fourth order, also known as "kurtosis", is defined as the fourth central moment of the set of data samples, divided by the fourth power of the standard deviation of the set of data samples. Kurtosis is a measure of how outlier-prone a distribution is. Further details about these statistical measures, and variants thereof, are disclosed in WO2012/175267, which is incorporated herein in its entirety by this reference.

For the avoidance of doubt, it is emphasized that step 121/121' may extract any combination of magnitude, heart rate, correlation value, and statistical shape measure for the supervised signals, and the detection and verification criteria of steps 122 and 122', respectively, may require any logic combination of the above-described CA tests to be fulfilled.

Figure 7:
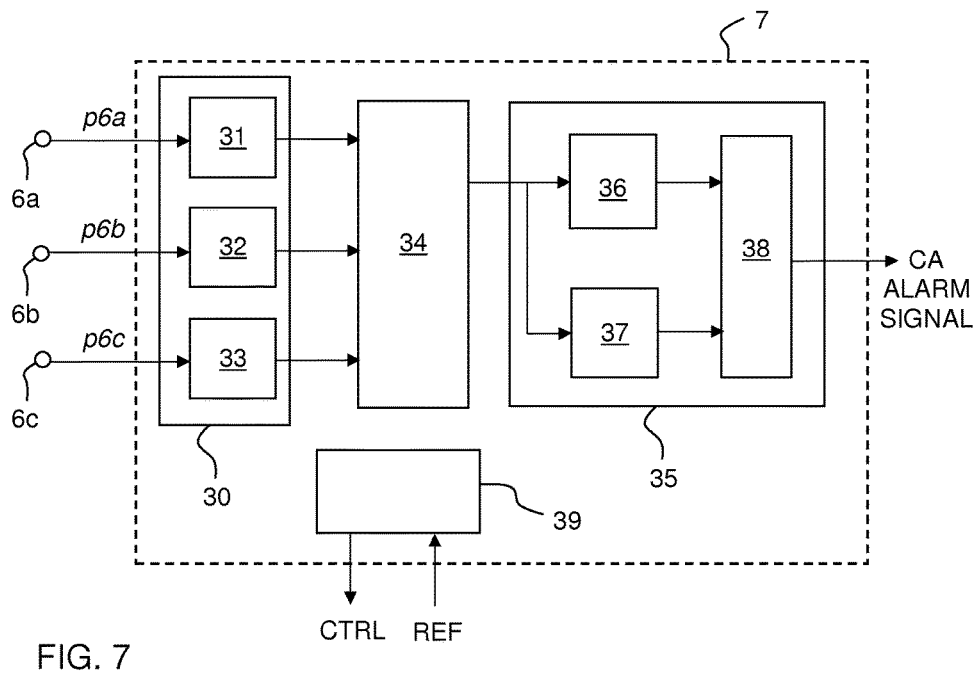
FIG. 7 is a block diagram of a structure for implementing the method in FIG. 5.

FIG. 7 is a block diagram of a structure for implementing the method of FIG. 5 in the device 7. In the illustrated embodiment, the device 7 includes an input block 30 with sub-blocks 31-33, a processing block 34, and an evaluation block 35, which includes a detection test sub-block 36, a verification test sub-block 37 and an alarm generation sub-block 38. Furthermore, a control block 39 is provided to synchronize the operation of blocks 30-38. Depending on implementation, the blocks 30-38 may be wired to exchange data as shown by arrows in FIG. 5, or the exchange of data may occur by intermediate data storage in and retrieval from an electronic memory (cf. MEM in FIG. 1).

It should be emphasized that the blocks in FIG. 7 may be implemented by hardware circuitry, by software executed on a processing unit, or by a combination of hardware circuitry and software. In one embodiment, the hardware circuitry/software is physically structured into the blocks (or modules) as shown in FIG. 7, e.g. the input block 30, the processing block 34, and the evaluation block 35. In another embodiment, the hardware circuitry/software is not physically structured into these blocks, but may conceptually be re-arranged into functionally equivalent blocks, or means for performing the function of the respective block.

In the illustrated example, the input block 30 implements step 110 in FIG. 5 and is arranged to obtain, by the respective sub-block 31, 32, 33, the venous, arterial and TF signals p6a, p6b, p6c from the sensors 6a, 6b, 6c and output a respective time-sequence of signal values. The input block 30 also implement step 120, i.e. the filtering of the signals p6a, p6b, p6c during the detection phase 100B. The input block 30 is controllable to switch the filtering on and off. The processing block 34 implements the viability checking phase 100A according to steps 112, 113 and 114 (cf. FIG. 6A), as well as the generation of the evaluation parameter values according to steps 121 and 121'. The detection test sub-block 36 implements steps 122, 123, 130 and 131, and the verification test sub-block 37 implements steps 121', 122', 123' and 131'. The alarm generation sub-block 38 implements step 140. Finally, the control block 39 implements the step of generating an external control signal CTRL for starting and stopping the blood pump 4 according to steps 115, 115', and optionally for changing the pumping rate of the blood pump to improve CA monitoring. The control block 39 also implements step 116, by selectively activating the detection test sub-block 36 and the verification test sub-block 37 and by controlling the input block 30 to switch the filtering on and off. Depending on the use of evaluation parameters in the detection phase 100B and verification phase 100C, respectively, the control block 39 may also actively control the processing block 34 to generate a specific set of evaluation parameters in each of the detection and verification phases 100B, 100C.

In the illustrated example, the control block 39 also implements the above-described estimation of the pumping rate, e.g. based on the reference signal REF. The resulting pumping rate may be used by the sub-block 36 for implementing CA test IV, or it may be utilized by the control block 39 for actively controlling the blood pump (via the control signal CTRL) to avoid overlap between the heart rate and a pump frequency.

In brief, the device 7 in FIG. 7 monitors the patient that is connected to a blood treatment apparatus for cardiac arrest (CA) based on one or more pressure signals. The device 7 implements the viability checking phase by causing the processing block 34 to repeatedly retrieve a signal value from each of the input sub-blocks 31-33 (step 110) and perform the viability test (step 112), until the viability checking phase is either successfully completed or aborted (step 114). During the viability checking phase, the processing block 34 may also be caused to configure the subsequent detection and/or verification phases (step 113). Then, the control block 39 enters the detection phase (step 111) by causing the blood pump 4 to be started (step 115), if not already started, and the filtering to be started in the input block 30 (step 120). The control block 39 also activates the processing block 34 and the detection test sub-block 36 to operate in the detection phase. The processing block 34 repeatedly obtains a signal value from one or more of the input sub-blocks 31-33 (the supervised signals) and computes the evaluation parameter value(s) for each supervised signal (step 121). The detection test sub-block 36 repeatedly evaluates the detection criterion, using the evaluation parameter value(s) generated by the processing block 34 (step 122). The repetitive operation of the processing block 34 and the detection test sub-block 36 continues if evaluation of the detection criterion is negative (not fulfilled). If the evaluation of the detection criterion is positive (fulfilled), the detection test sub-block 36 evaluates the confidence level (step 130) and either triggers the sub-block 38 to generate the CA alarm signal (step 140) or indicates that the device 7 should enter the verification phase (step 131). The latter event triggers the control block 39 to stop the blood pump 4 (step 115'), to stop the filtering in the input block 30 and to activate the processing block 34 and the verification test sub-block 37 to operate in the verification phase. The processing block 34 repeatedly obtains a signal value from one or more of the input sub-blocks 31-33 (the supervised signals) and computes the evaluation parameter value(s) for each supervised signal (step 121'). The verification test sub-block 37 repeatedly evaluates the verification criterion, using the evaluation parameter value(s) generated by the processing block 34 (step 122'). If the evaluation of the verification criterion is positive (fulfilled), the verification test sub-block 37 triggers the sub-block 38 to generate the CA alarm signal (step 140). If the evaluation of the verification criterion is negative (not fulfilled), the verification test sub-block 37 indicates that the device 7 should enter either the detection phase or the viability checking phase (step 131'). If the device 7 is to enter the detection phase, this indication triggers the control block 39 to start the blood pump (step 115) and the filtering in the input block 30. The control block 39 also activates the processing block 34 and the detection test sub-block 36 to operate in the detection phase. If the device 7 is to enter the viability checking phase, this indication causes the control block 39 to keep the blood pump 4 stopped and triggers the processing block 34 to perform the viability checking phase (steps 112, 113, 114).

Figure 8:
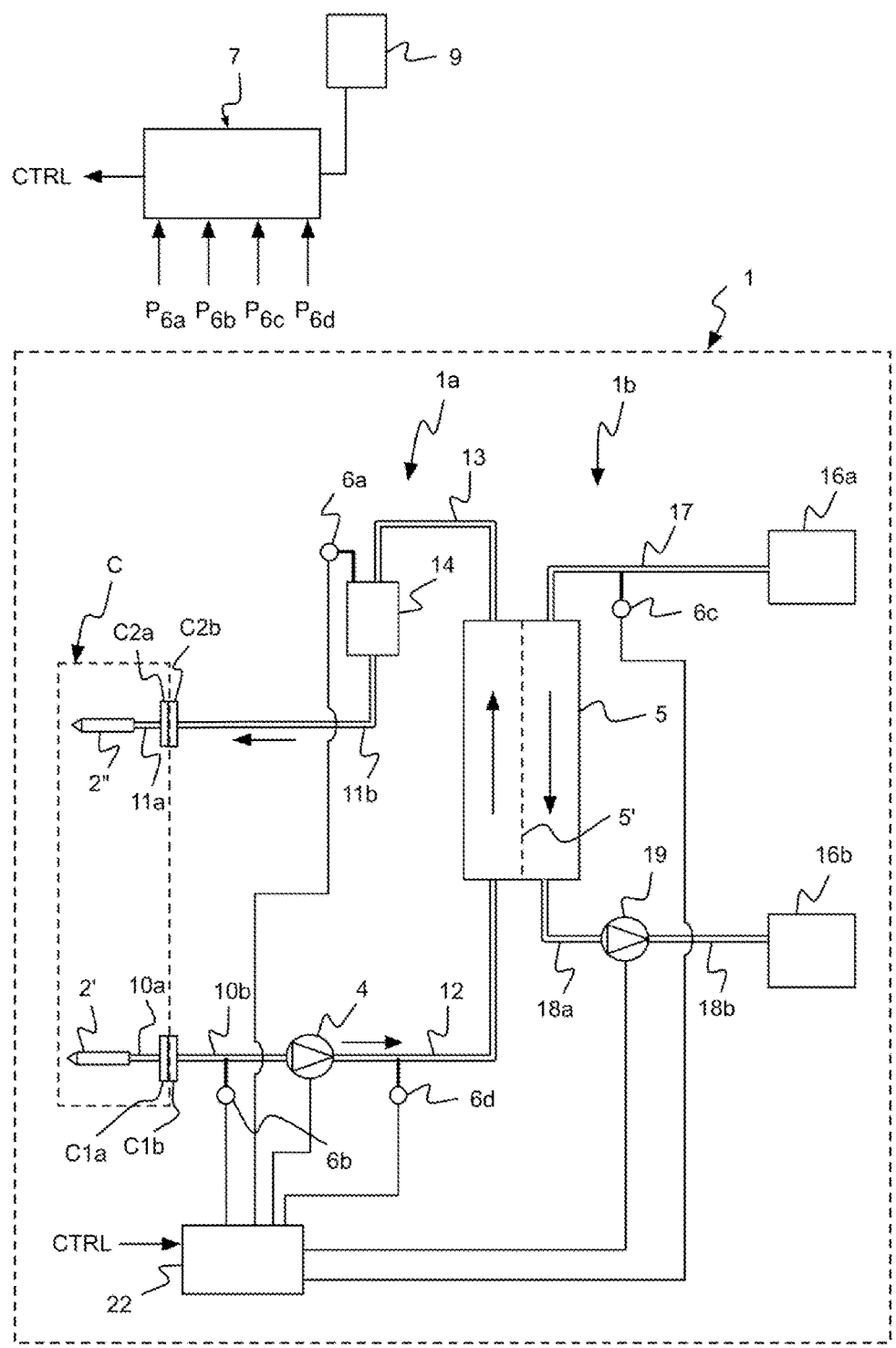
FIG. 8 is a schematic view of a dialysis system and an inventive monitoring device.

FIG. 8 serves to give a more detailed example of a blood treatment apparatus 1, implemented as a system for hemodialysis treatment, and the practical use of the inventive CA monitoring. The apparatus 1 comprises an EC circuit 1a which includes a connection system C for establishing fluid communication between the EC circuit 1a and the vascular system of a patient. The connection system C comprises an arterial access device 2' (here in the form of an arterial needle), a connection tube segment 10a and a connector C1a. The connection system C also comprises a venous access device 2" (here in the form of a venous needle), a connection tube segment 11a and a connector C2a. The connectors C1a, C2a are arranged to provide a releasable or permanent engagement with a corresponding connector C1b, C2b. The connectors C1a, C1b, C2a, C2b may be of any known type. In certain implementations, the connectors C1a, C1b, C2a, C2b may be omitted, whereby the connection system C consists of the access devices 2', 2".

In FIG. 8, the EC circuit 1a further comprises an arterial tube segment 10b, and a blood pump 4 which may be of peristaltic type. On the arterial side of the blood pump 4 there is an arterial pressure sensor 6b which measures the pressure upstream of the pump 4 in the arterial tube segment 10b. The pump 4 forces the blood, via a tube segment 12, to the blood-side of the dialyzer 5. The illustrated apparatus 1 is additionally provided with a pressure sensor 6d ("system pressure sensor") that measures the pressure between the blood pump 4 and the dialyzer 5. The blood is led via a tube segment 13 from the blood-side of the dialyzer 5 to a venous drip chamber or deaeration chamber 14 and from there back to the connection system C via a venous tube segment 11b and the connector C2b. A venous pressure sensor 6a is provided to measure the pressure on the venous side of the dialyzer 5, here in the venous drip chamber 14.

In the example of FIG. 8, the venous side of the EC circuit 1a is made up of tube segment 12, the blood-side of the dialyzer 5, tube segment 13, venous drip chamber 14, tube segment 11b, connectors C2a, C2b, tube segment 11a, and the venous access device 2", and the arterial side is made up of tube segment 10b, connectors C1a, C1b, tube segment 10a, and the arterial access device 2'.

Both the arterial needle 2' and the venous needle 2" are configured to be connected to a vascular access (cf. 3 in FIG. 1). Depending on the type of vascular access, other types of access devices may be used instead of needles, e.g. catheters. The vascular access 3 may be of any suitable type, including different types of venovenous (VV) blood accesses and different types of arteriovenous (AV) access, such as a graft or a fistula.

The apparatus 1 also comprises a TF circuit 1b, here exemplified as a source 16a of treatment fluid ("dialysis fluid"), a tube segment 17, a TF-side of the dialyzer 5, a tube segment 18a, a TF fluid pump 19, a tube segment 18b, and an outlet/drain 16b. A TF pressure sensor 6c is provided to measure the fluid pressure in the TF circuit 1b. It is to be understood that FIG. 8 is schematic and exemplary, and that the TF circuit 1b may include other components, such as further pumps, further flow paths, flow-controlling valves, chambers, further pressure sensors, etc. The source 16a may comprise a fluid generation unit that produces the treatment fluid from one or more concentrates and water, and optionally performs degassing and heating of the treatment fluid and controls its flow rate and pressure.

The apparatus 1 further comprises a central control unit 22 that controls the operation of the apparatus 1. In FIG. 8, the control unit 22 is connected to operate the pumps 4, 19, various valves (not shown), clamping devices (not shown), and to acquire data from the pressure sensors 6a-6d. Although not shown or discussed further it is to be understood that the control unit 22 may implement many different functions, e.g. various safety functions, controlling the temperature, composition, pressure and flow rate of the treatment fluid, controlling additional pumps, etc.

In the illustrated example, the monitoring device 7 is connected by data lines to the pressure sensors 6a-6d so as to acquire pressure signals p6a, p6b, p6c and p6d. The device 7 is also connected by a data line to the control unit 22 for transmitting the control signal CTRL that may, e.g., cause the control unit 22 to change the revolution speed of the blood pump 4, or cause the control unit 22 to start and stop the blood pump 4 and possibly the TF fluid pump 19.

The device 7 is also be tethered or wirelessly connected to the CA alarm device 9. The device 7 may be connected to further devices (not shown), e.g. a display for displaying information, an interface (keyboard, mouse, touch screen, etc) for accepting user input etc. The device 7 may be implemented as a separate unit connected to the apparatus 1 (as shown), or it may be incorporated as part of the apparatus 1, e.g. as part of the control device 22.

Figure 10:
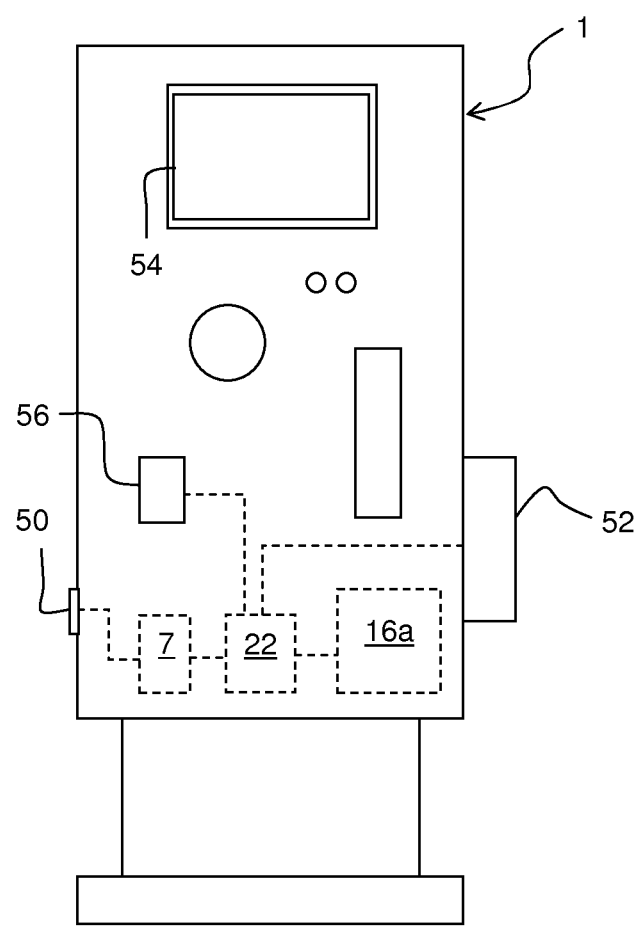
FIG. 10 is a front view of a dialysis monitor equipped for revival of a patient suffering from cardiac arrest.

FIG. 10 exemplifies an apparatus 1 for blood treatment, shown in front view and implemented as a dialysis monitor, which is configured to facilitate on-site revival and treatment of a dialysis patient that suffers from cardiac arrest. Apart from the components described below, the monitor 1 may be of any conventional design known to the skilled person. The dashed lines indicate a few internal components of the dialysis monitor 1, including the central control unit 22 and the monitoring device 7 as described above in relation to FIG. 8. The monitoring device 7 is connected to a connector/communication device 50 for supplying the CA alarm signal to the CA alarm device (not shown), by wired or wireless communication. Reference numeral 52 indicates revival equipment for defibrillation and/or cardiopulmonary resuscitation which is removably attached to the monitor 1. In a first variant, the revival equipment 52 is attached to the patient during the dialysis treatment and is activated by the control unit 22 if the monitoring device 7 generates the CA alarm signal and, preferably, if the staff confirms to the monitor 1 that the patient indeed needs to be revived. In a second variant, the revival equipment 52 is configured to be detached from the monitor 1 by the clinical staff and used in the event of a cardiac arrest and may or may not be controlled by the control unit 22. The control unit 22 may also be operable to control the source 16a of dialysis fluid to lower the temperature of the dialysis fluid, for cooling the patient as discussed in the foregoing. The cooling may e.g. be automatically initiated when the revival equipment 52 is activated (first variant) or when the revival equipment 52 is detached from the monitor 1 (second variant). Alternatively, the cooling may be initiated on command by the clinical staff, e.g. via touch screen 54 or a mechanical switch (not shown). The control unit 22 may also be operable to control the source 16a to change the composition of the dialysis fluid, if the monitoring device 7 generates the CA alarm signal. The purpose of the change of composition is to promote revival and recovery of the patient by changing the composition of the blood pumped to the patient. Alternatively or additionally, the control unit 22 is operatively connected to a blood interfacing device 56 included in the EC circuit and configured to directly interface with the blood pumped to the patient. The device 56 may be a syringe or pump for connection to the blood line set and operable to inject a substance into the blood, or a gas exchanger for connection to the blood line set and operable to change the partial pressures of one or more gaseous components (e.g. $O_2$, $CO_2$) in the blood.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For the avoidance of doubt, the inventive CA monitoring may be implemented to operate on a single pressure signal, using any of the above-described CA tests except CA tests II and VI which inherently require at least two pressure signals.

Furthermore, the pressure signal(s) may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, etc. It is also understood that the pressure sensor may be configured to measure a quantity that is equivalent to pressure and represents the pressure waves that are generated by the heartbeats in the subject, such as a change in volume or a change in flow rate.

Even if the inventive CA monitoring technique has been described in relation to a blood treatment apparatus for hemodialysis (HD) treatment, it is equally applicable in a blood treatment apparatus for ultrafiltration (UF), hemofiltration (HF) or hemodiafiltration (HDF). The inventive technique may be applicable for CA monitoring in connection with other types of blood processing, such as in a blood processing apparatus for plasmapheresis, bloodbanking, blood fraction separation (e.g. cells) of donor blood, apheresis, extracorporeal blood oxygenation, assisted blood circulation and extracorporeal liver support/dialysis.

The inventive technique is also applicable for CA monitoring in blood treatments performed with single-needle access or with central venous catheter (CVC). It can be noted that while CA monitoring is critical also in treatments with single-needle access or with double lumen catheters, needle dislodgment monitoring is not.

In treatments with single-needle access or CVC, the heart pulses will typically not (but may) be present in the arterial and venous pressure signals at the same time, but come in an alternating manner, since the single-needle access requires the blood processing apparatus to operate with alternating blood withdrawal and blood return through the single needle (or CVC). The CA tests described hereinabove may nevertheless be applied for both of these pressure signals (or other pressure signals), if desired, by treating the sections that should contain heart pulses in the respective supervised signal as recorded simultaneously. For example, to enable CA test VI, a segment of the arterial signal acquired during blood withdrawal may be correlated with a segment of the venous signal acquired during a preceding or subsequent blood return. In another example, CA test I may be regarded as fulfilled if the magnitude indicates disappearance of heart pulses in both a segment in the arterial signal acquired during blood withdrawal and in a segment of the venous signal acquired during a preceding or subsequent blood return. CA tests II, III, IV, V and VI may be modified correspondingly.

Figure 9A:
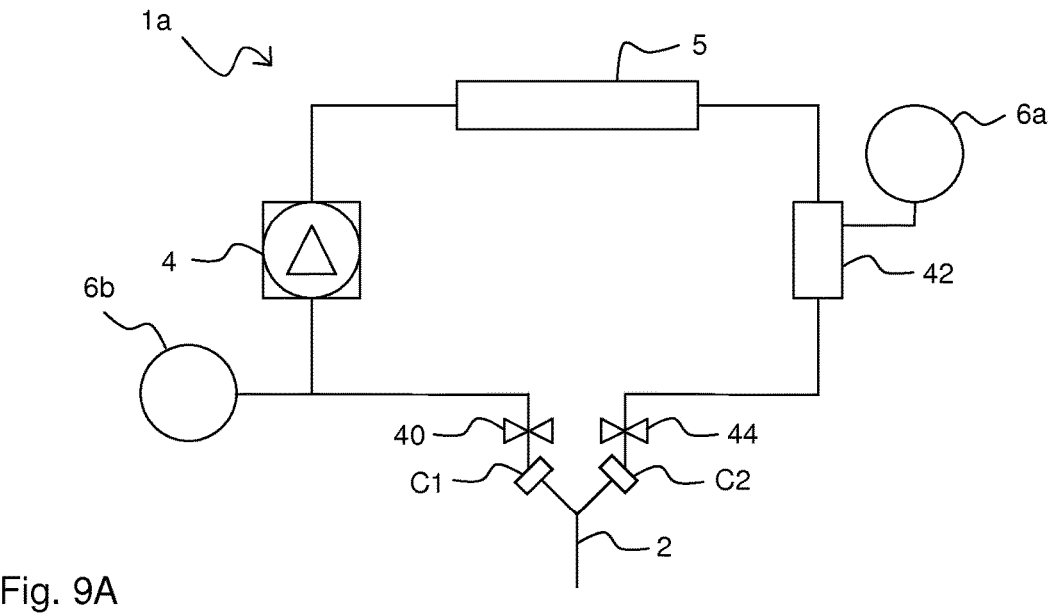
FIGS. 9A-9B are schematic views of dialysis systems with a single access device.
Figure 9B:
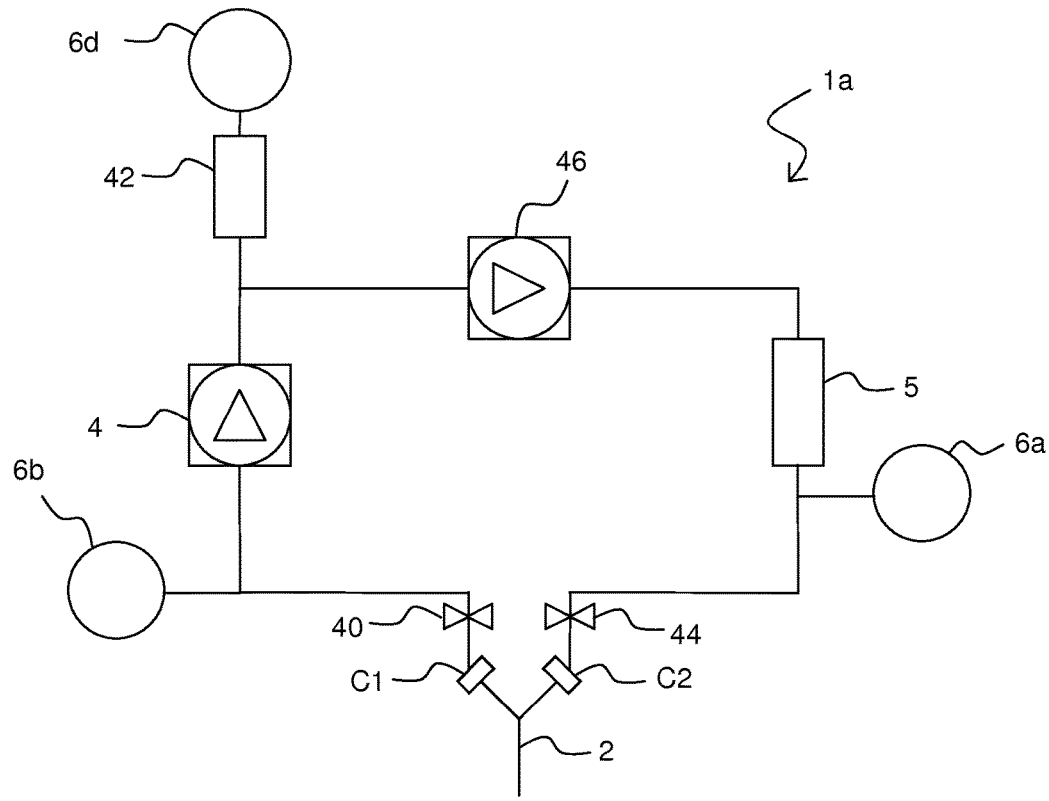

Thus, any one of the above-mentioned first, second and third concepts (FIGS. 2A-2C) may be implemented in a dialysis system that is connected to the patient by a single access device ("single-access system"). Examples will be described below in relation to two different types of single-access systems: a "pump/clamp system" shown in FIG. 9A and a "double pump system" shown in FIG. 9B. It should be noted that the block diagrams in FIGS. 9A-9B are schematic and focus on principal components in the EC circuit 1a. For example, the TF circuit has been omitted.

Looking at FIG. 9A, the pump/clamp system contains a single access device 2, which is connected by connectors C1, C2 to an arterial blood line and a venous blood line, respectively. The arterial blood line extends from the connector C1 to the dialyzer 5 and includes, in hydraulic order, an arterial-side clamp 40, an arterial pressure sensor 6b and a blood pump 4. The venous blood line extends from the dialyzer 5 to the connector C2 and includes, in hydraulic order, a container 42 (denoted "compliance vessel") and a venous-side clamp 44, where a venous pressure sensor 6a is connected to measure the pressure in the vessel 42. The operation of the clamps 40, 44 and the blood pump 4 are controlled by a control unit (not shown), which operates the system to alternate between blood withdrawal and blood return. During blood withdrawal, clamp 40 is opened, clamp 44 is closed and blood is pumped from the patient via the access device 2 through the dialyzer 5 and is stored in the vessel 42. During blood return, clamp 40 may be closed, clamp 44 is opened and blood flows from the vessel 42 through the venous blood line back to the patient via the access device 2. The pump 4 should be activated only during blood withdrawal. The clamp 40 may be omitted if the pump 4 is occluding when stopped (i.e. prevents backflow of blood towards the access device 2). The vessel 42 may alternatively be located in the arterial blood line between the pump 4 and the dialyzer 5. The structure and operation of the pump/clamp system, and variants thereof, is well-known to the skilled person.

Irrespective of how the blood pump 4 is operated in the dialysis system of FIG. 9A, the CA monitoring may be implemented with a detection phase and a verification phase. During the detection phase, the dialysis system repeatedly performs blood withdrawal and blood return, and the CA monitoring (e.g. implemented by device 7 in FIG. 7) evaluates one or more of the signals from the sensors 6a, 6b. During the verification phase, the dialysis system is disabled (the pump 4 is stopped) and the CA monitoring evaluates one or more of the signals from the sensors 6a, 6b.

The present Applicant has found that it is possible to perform the verification phase without having to disable the dialysis system, provided that the pump 4 is only activated during blood withdrawal. In one example, the dialysis system is operated to repeatedly perform blood withdrawal and blood return, and the CA monitoring is operated in the detection phase by evaluating the venous and/or arterial pressure signals. The detection phase is implemented depending on the availability of heart pulses. If the clamps 40, 44 are opened and closed in opposite phases, the heart pulses will come in an alternating manner in the arterial and venous pressure signals. If clamp 40 is omitted, the heart pulses will be present in the arterial pressure signal during both blood withdrawal and blood return. In the verification phase, the dialysis system continues to repeatedly perform blood withdrawal and blood return, and the CA monitoring evaluates one or more of the pressure signals only during blood return. In one implementation, only the venous pressure signal is evaluated during the verification phase. In another implementation, the clamp 40 is opened during blood return, or omitted altogether, such that pressure waves from heartbeats (if present) reach also the arterial sensor 6b during blood return, and both the arterial and venous pressure signals are evaluated during the verification phase.

In yet another embodiment, the CA monitoring is only performed during blood return. This means that the CA monitoring is implemented without separate detection and verification phases. Rather, the CA monitoring may be regarded as being implemented without a detection phase but with a verification phase, since the CA incidents are detected when the pump 4 is temporarily stopped during blood return.

Turning now to the example in FIG. 9B, the double pump system contains a single access device 2, which is connected by connectors C1, C2 to an arterial blood line and a venous blood line, respectively. The arterial blood line extends from the connector C1 to the dialyzer 5 and includes, in hydraulic order, an arterial-side clamp 40, an arterial pressure sensor 6b, a first (occluding) blood pump 4, a container 42 ("compliance vessel") and a second (occluding) blood pump 46. A system pressure sensor 6d is connected to measure the pressure in the vessel 42. The venous blood line extends from the dialyzer 5 to the connector C2 and includes, in hydraulic order, a venous pressure sensor 6a and a venous-side clamp 44. The operation of the clamps 40, 44 and the blood pumps 4, 46 are controlled by a control unit (not shown), which operates the system to alternate between blood withdrawal and blood return. During blood withdrawal, clamp 40 is opened, clamp 44 is closed, second blood pump 46 is stopped, and the first pump 4 is activated to pump blood from the patient via the access device 2 into the vessel 42. During blood return, clamp 40 may be closed, clamp 44 is opened, the first pump 4 is stopped, and the second pump 46 is activated to pump blood from the vessel 42 through the venous blood line back to the patient via the access device 2. The clamp 40 may be omitted if the first pump 4 is occluding (i.e. prevents backflow of blood). The structure and operation of the double pump system, and variants thereof, is well-known to the skilled person.

In the dialysis system of FIG. 9B, the CA monitoring may be implemented with a detection phase and a verification phase. During the detection phase, the dialysis system repeatedly performs blood withdrawal and blood return, and the CA monitoring (e.g. implemented by device 7 in FIG. 7) evaluates one or more of the signals from the sensors 6a, 6b. During the verification phase, the dialysis system is disabled (the pumps 4, 46 are stopped) and the CA monitoring evaluates one or more of the signals from the sensors 6a, 6b.

The present Applicant has realized that the verification phase may be performed during a switching period between blood withdrawal and blood return, provided that at least one of the clamps 40, 44 is opened during the switching period. In the switching period there are no disturbances from the pumps 4, 46 in the pressure signals. Thus, the verification phase may be performed during regular operation of the dialysis system. In one example, the dialysis system is operated to repeatedly perform blood withdrawal and blood return, and the CA monitoring is operated in the detection phase by evaluating the venous and/or arterial pressure signals. The detection phase will be implemented depending on the availability of heart pulses. If the clamps 40, 44 are opened and closed in opposite phases, the heart pulses will come in an alternating manner in the arterial and venous pressure signals. If clamp 40 is omitted, the heart pulses will be present in the arterial pressure signal during both blood withdrawal and blood return. In the verification phase, the dialysis system continues to repeatedly perform blood withdrawal and blood return, and the CA monitoring evaluates one or more of the pressure signals during the switching phase. Thus, the verification phase is executed while the dialysis system continues to perform blood treatment, by verifying if the heart pulses are indeed absent in the supervised signal(s) that are acquired during one or more switching periods. It is conceivable that the dialysis system is controlled to selectively increase the length of the switching period when the CA monitoring enters the verification phase.

In another embodiment, the CA monitoring is only performed during the switching periods, i.e. when the pumps 4, 46 are stopped. In this embodiment, the CA monitoring is implemented without separate detection and verification phases. Thus, the CA monitoring may be regarded as being implemented without a detection phase but with a verification phase, since the CA incidents are detected when the pumps 4, 46 are stopped.

The invention claimed is:

1. A monitoring device, comprising:
an input block configured to obtain a first pressure signal from a first pressure sensor and a second pressure signal from a second pressure sensor, the first and second pressure sensors arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and includes at least one blood pumping device operable to pump blood from the vascular system through the blood processing unit and back to the vascular system;
a processing block configured to repeatedly process the first pressure signal and the second pressure signal for generation of a time-sequence of parameter values indicative of pressure pulsations originating from heartbeats in the subject; and
an evaluation block configured to (i) evaluate the parameter values according to a detection criterion for cardiac arrest, which is set to detect a disappearance of the pressure pulsations originating from the heartbeats in the first pressure signal and the second pressure signal, and, (ii) if the detection criterion is fulfilled, generate an alarm signal that signals a cardiac arrest in the subject.

2. The monitoring device of claim 1, wherein the first pressure sensor is located on a venous side of an extracorporeal circuit of the extracorporeal blood processing apparatus, and the second pressure sensor is located on an arterial side of the extracorporeal circuit.

3. The monitoring device of claim 1, wherein the monitoring device is further configured to generate an alarm signal for needle dislodgement upon a needle dislodgement, and wherein the alarm signal for cardiac arrest is distinguished from the alarm signal for needle dislodgement.

4. The monitoring device of claim 1, wherein the time-sequence of parameter values includes a time-sequence of first rate values that represent a rate of the pressure pulsations originating from the heartbeats in the first pressure signal, and a time-sequence of second rate values that represent a rate of the pressure pulsations originating from the heartbeats in the second pressure signal, and wherein the detection criterion involves identifying a difference between the first and second rate values.

5. The monitoring device of claim 1, wherein the time-sequence of parameter values includes a time-sequence of correlation values that represent a degree of correlation between the first and second pressure signals, and wherein the detection criterion involves comparing the correlation values to a correlation threshold.

6. The monitoring device of claim 1, wherein the time-sequence of parameter values includes a time-sequence of magnitude values that represent a magnitude of the pressure pulsations originating from the heartbeats in at least the first pressure signal, and wherein the detection criterion involves comparing the magnitude values to a magnitude threshold.

7. The monitoring device of claim 1, wherein the time-sequence of parameter values includes a time-sequence of rate values that represent a rate of the pressure pulsations originating from the heartbeats in at least the first pressure signal; and wherein the detection criterion involves at least one of: identifying a sudden change in the time-sequence of rate values; identifying, based on the time-sequence of rate values, that the rate of the pressure pulsations is substantially equal to a frequency of said at least one blood pumping device; and identifying, based on the time-sequence of rate values, that the rate of pressure pulsations is outside a predefined range, which defines physiological limits for the rate of heartbeats in the subject.

8. The monitoring device of claim 1, wherein the time-sequence of the parameter values includes a time-sequence of statistical values that represent the shape of at least the first pressure signal and are computed as a statistical measure for signal values within a time window in at least the first pressure signal, and wherein the detection criterion involves comparing the statistical values to a statistics threshold.

9. The monitoring device of claim 1, wherein the evaluation block includes a detection test sub-block and a verification test sub-block, wherein the monitoring device is configured to, during operation of said at least one blood pumping device, cause the detection test sub-block to evaluate the time-sequence of parameter values according to the detection criterion, and wherein the monitoring device is configured to, if the detection criterion is fulfilled, stop said at least one blood pumping device and initiate the verification test sub-block, and wherein the verification test sub-block is configured to, upon said initiation, evaluate at least the first pressure signal for absence of the pressure pulsations originating from heartbeats in the subject when said at least one blood pumping device is stopped and, upon detection of absence of the pressure pulsations, cause the evaluation block to generate the alarm signal that signals a cardiac arrest in the subject.

10. The monitoring device of claim 9, wherein the verification test sub-block is configured to evaluate at least the first pressure signal for absence of the pressure pulsations originating from heartbeats in the subject based on the time sequence of parameter values that are generated by the processing block after said at least one blood pumping device has been stopped.

11. The monitoring device of claim 9, wherein the input block is configured to perform a preparatory filtering to suppress pressure pulsations that originate from said at least one blood pumping device in at least the first pressure signal, and wherein the monitoring device is configured to change or disable the preparatory filtering in the input block when the verification test sub-block is initiated.

12. The monitoring device of claim 9, wherein the detection test sub-block is further configured to, if the detection criterion is fulfilled, evaluate a confidence level of the thus-fulfilled detection criterion, wherein the detection test sub-block is configured to cause the evaluation block to generate the alarm signal if the confidence level is deemed sufficient, and wherein the monitoring device is configured to initiate the verification test sub-block if the confidence level is deemed insufficient.

13. The monitoring device of claim 9, wherein the verification test sub-block is configured to, if being unable to detect absence of the pressure pulsations in at least the first pressure signal, initiate a configuration process for setting the detection criterion based on at least the first pressure signal.

14. The monitoring device of claim 1, which is operable in a viability checking phase to enable the monitoring device for detection of cardiac arrest, wherein the viability checking phase includes: comparing a magnitude of the pressure pulsations that originate from the heartbeats in at least the first pressure signal to a viability threshold; and enabling the monitoring device for detection of cardiac arrest provided that the magnitude exceeds the viability threshold.

15. The monitoring device of claim 14, wherein the viability checking phase further includes selecting at least the first pressure signal among a plurality of pressure signals obtained from a plurality of pressure sensors in the extracorporeal blood processing apparatus, based on the magnitude of the pressure pulsations originating from the heartbeats in the respective pressure signal.

16. The monitoring device of claim 14, which is configured to perform the viability checking phase such that said at least one blood pumping device is stopped during at least part of the viability checking phase.

17. The monitoring device of claim 1, wherein the extracorporeal blood processing apparatus is connected to the vascular system via a single access device and is configured to operate in a repeating sequence of a blood withdrawal period in which a first blood pumping device is operated to draw blood from the vascular system via the access device, a blood return period in which a second blood pumping device is operated to pump the blood back to the vascular system via the access device, and a switching period between the blood withdrawal and blood return periods in which the first and second blood pumping devices are stopped, wherein the processing block is configured to generate the time-sequence of parameter values during the switching period, and wherein the evaluation block is configured to evaluate the parameter values generated during the switching period for detection of cardiac arrest.

18. The monitoring device of claim 1, wherein the extracorporeal blood processing apparatus is connected to the vascular system via a single access device and is configured to operate in a repeating sequence of a blood withdrawal period in which said at least one blood pumping device is operated to draw blood from the vascular system via the access device into a container, a blood return period in which said at least one blood pumping device is stopped and the blood flows from the container back into the vascular system via the access device, and wherein the processing block is configured to generate the time-sequence of parameter values during the blood return period, and wherein the evaluation block is configured to evaluate the parameter values generated during the blood return period for detection of cardiac arrest.

19. The monitoring device of claim 1, which is configured to modify the detection criterion as a function of one or more operating parameters of the extracorporeal blood processing apparatus.

20. The monitoring device of claim 1, wherein the first pressure sensor is arranged upstream of the blood processing unit and said at least one blood pumping device in an extracorporeal blood circuit in the extracorporeal blood processing apparatus, and wherein the pressure pulsations originating from heartbeats in the subject are superimposed on a baseline pressure level in the first pressure signal, wherein the evaluation block is configured to generate the alarm signal only in absence of a recent change in the baseline pressure level.

21. The monitoring device of claim 1, wherein the first pressure sensor is one of (i) a pressure sensor arranged downstream of said at least one blood pumping device and the blood processing unit in an extracorporeal blood circuit in the extracorporeal blood processing apparatus, (ii) a pressure sensor arranged upstream of said at least one blood pumping device and the blood processing unit in the extracorporeal blood circuit, and (iii) a pressure sensor arranged in a treatment fluid supply system for pumping a treatment fluid through the blood processing unit.

22. A monitoring device, comprising:
means for obtaining a first pressure signal from a first pressure sensor and a second pressure signal from a second pressure sensor, the first and second pressure sensors arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and includes at least one blood pumping device operable to pump blood from the vascular system through the blood processing unit and back to the vascular system;
means for repeatedly processing the first pressure signal and the second pressure signal for generation of a time-sequence of parameter values indicative of pressure pulsations originating from heartbeats in the subject;
means for evaluating the parameter values according to a detection criterion for cardiac arrest, which is set to detect a disappearance of the pressure pulsations originating from the heartbeats in the first pressure signal and the second pressure signal; and
means for generating, if the detection criterion is fulfilled, an alarm signal that signals a cardiac arrest in the subject.

23. A monitoring device, comprising:
an input block configured to obtain a first pressure signal from a first pressure sensor and a second pressure signal from a second pressure sensor, the first and second pressure sensors arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and includes at least one blood pumping device operable to pump blood from the vascular system through the blood processing unit and back to the vascular system; and
a signal processor configured to (i) repeatedly process the first pressure signal and the second pressure signal for generation of a time-sequence of parameter values indicative of pressure pulsations originating from heartbeats in the subject, (ii) evaluate the parameter values according to a detection criterion for cardiac arrest, which is set to detect a disappearance of the pressure pulsations originating from the heartbeats in the first pressure signal and the second pressure signal, and (iii) generate, if the detection criterion is fulfilled, an alarm signal that signals a cardiac arrest in the subject.

24. An apparatus for extracorporeal blood processing, said apparatus comprising:
an extracorporeal blood circuit for connection to the vascular system of a subject;
a blood processing unit in the extracorporeal blood circuit;
at least one blood pumping device in the extracorporeal blood circuit, the at least one blood pumping device operable to pump blood from the vascular system through the blood processing unit and back to the vascular system;
a treatment fluid supply system operable to pump a treatment fluid through the blood processing unit; and
a pressure sensor arranged in one of the extracorporeal blood circuit and the treatment fluid supply system to detect pressure variations in one of the blood and the treatment fluid, said apparatus further comprising the monitoring device as set forth in claim 23.

25. The apparatus of claim 24, further comprising revival equipment for cardiopulmonary resuscitation and/or defibrillation.

26. The apparatus of claim 25, which is operable to activate the revival equipment when the monitoring device has generated the alarm signal that signals a cardiac arrest in the subject.

27. The apparatus of claim 24, which is operable to control the treatment fluid supply system to decrease the temperature of the treatment fluid, so as to decrease the body temperature of the subject, when the monitoring device has generated the alarm signal that signals a cardiac arrest in the subject.

28. The apparatus of claim 24, which is operable to control, when the monitoring device has generated the alarm signal that signals a cardiac arrest in the subject, at least one of the treatment fluid supply system and the extracorporeal blood circuit to change the composition of the blood pumped to the vascular system of the subject.

29. A monitoring method, comprising:
obtaining a first pressure signal from a first pressure sensor and a second pressure signal from a second pressure sensor, the first and second pressure sensors arranged in an extracorporeal blood processing apparatus to detect pressure variations in a fluid which is pumped through a blood processing unit in the extracorporeal blood processing apparatus, wherein the extracorporeal blood processing apparatus is connected to a vascular system of a subject and includes at least one blood pumping device operable to pump blood from the vascular system through the blood processing unit and back to the vascular system;
processing the first pressure signal and the second pressure signal for generation of a time-sequence of parameter values indicative of pressure pulsations originating from heartbeats in the subject;
evaluating the parameter values according to a detection criterion for cardiac arrest, which is set to detect a disappearance of the pressure pulsations originating from the heartbeats in the first pressure signal and the second pressure signal; and
generating, if the detection criterion is fulfilled, an alarm signal that signals a cardiac arrest in the subject.

30. The monitoring method of claim 29, wherein the first pressure sensor is arranged on a venous side of an extracorporeal circuit of the extracorporeal blood processing apparatus, and wherein the second pressure sensor is arranged on an arterial side of the extracorporeal circuit.

31. The monitoring method of claim 29, which includes generating an alarm signal for needle dislodgement upon a of needle dislodgement, and wherein the alarm signal for cardiac arrest is distinguished from the alarm signal for needle dislodgement.

32. The monitoring method of claim 29, wherein the time-sequence of parameter values includes a time-sequence of first rate values that represent a rate of the pressure pulsations originating from the heartbeats in the first pressure signal, and a time-sequence of second rate values that represent a rate of the pressure pulsations originating from the heartbeats in the second pressure signal; and wherein the detection criterion involves identifying a difference between the first and second rate values.

33. The monitoring method of claim 29, wherein the time-sequence of parameter values includes a time-sequence of correlation values that represent a degree of correlation between the first and second pressure signals, and wherein the detection criterion involves comparing the correlation values to a correlation threshold.

34. The monitoring method of claim 29, wherein the time-sequence of parameter values includes a time-sequence of magnitude values that represent a magnitude of the pressure pulsations originating from the heartbeats in at least the first pressure signal, and wherein the detection criterion involves comparing the magnitude values to a magnitude threshold.

35. The monitoring method of claim 29, wherein the time-sequence of parameter values includes a time-sequence of rate values that represent a rate of the pressure pulsations originating from the heartbeats in at least the first pressure signal; and wherein the detection criterion involves at least one of: (i) identifying a sudden change in the time-sequence of rate values; identifying, based on the time-sequence of rate values, that the rate of the pressure pulsations is substantially equal to a frequency of said at least one blood pumping device; or (ii) identifying, based on the time-sequence of rate values, that the rate of pressure pulsations is outside a predefined range, which preferably defines physiological limits for the rate of heartbeats in the subject.

36. The monitoring method of claim 29, wherein the time-sequence of parameter values includes a time-sequence of statistical values that represent the shape of at least the first pressure signal and are computed as a statistical measure for signal values within a time window in at least the first pressure signal, and wherein the detection criterion involves comparing the statistical values to a statistics threshold.

37. The monitoring method of claim 29, which is operable in a detection phase, in which the time-sequence of parameter values is evaluated according to the detection criterion during operation of said at least one blood pumping device, wherein the monitoring method further comprises, if the detection criterion is fulfilled, stopping said at least one blood pumping device and entering a verification phase, in which at least the first pressure signal is evaluated for absence of the pressure pulsations originating from heartbeats in the subject, and wherein the alarm signal is generated if the verification phase indicates an absence of the pressure pulsations originating from heartbeats in the subject.

38. The monitoring method of claim 37, wherein the verification phase evaluates at least the first pressure signal for absence of the pressure pulsations originating from heartbeats in the subject based on the time sequence of parameter values that are generated by the step of processing after said at least one blood pumping device has been stopped.

39. The monitoring method of claim 37, wherein at least the first pressure signal is subjected to a preparatory filtering during the detection phase to suppress pressure pulsations that originate from said at least one blood pumping device, and wherein the filtering is changed or disabled during the verification phase.

40. The monitoring method of claim 37, wherein the detection phase further includes, if the detection criterion is fulfilled, a step of evaluating a confidence level of the thus-fulfilled detection criterion, wherein the alarm signal is generated if the confidence level is deemed sufficient, and wherein the monitoring method enters the verification phase if the confidence level is deemed insufficient.

41. The monitoring method of claim 37, wherein the verification phase, if unable to indicate an absence of the pressure pulsations originating from heartbeats in the subject, initiates a configuration process for setting the detection criterion based on at least the first pressure signal.

42. The monitoring method of claim 37, which is operable in a viability checking phase to enable the monitoring method for detection of cardiac arrest, wherein the viability checking phase includes: comparing a magnitude of the pressure pulsations that originate from the heartbeats in at least the first pressure signal to a viability threshold; and enabling the monitoring method for detection of cardiac arrest provided that the magnitude exceeds the viability threshold.

43. The monitoring method of claim 42, which executes the viability checking phase such that said at least one blood pumping device is stopped during at least part of the viability checking phase.

44. The monitoring method of claim 29, further comprising: selecting at least the first pressure signal among a plurality of pressure signals obtained from a plurality of pressure sensors in the extracorporeal blood processing apparatus, based on a magnitude of the pressure pulsations originating from the heartbeats in the respective pressure signal.

45. The monitoring method of claim 29, wherein the extracorporeal blood processing apparatus is connected to the vascular system via a single access device and operates in a repeating sequence of a blood withdrawal period in which a first blood pumping device is operated to draw blood from the vascular system via the access device, a blood return period in which a second blood pumping device is operated to pump the blood back to the vascular system via the access device, and a switching period between the blood withdrawal and blood return periods in which the first and second blood pumping devices are stopped, wherein the monitoring method generates the time-sequence of parameter values during the switching period, and evaluates the parameter values that are generated during the switching period for detection of cardiac arrest.

46. The monitoring method of claim 29, wherein the extracorporeal blood processing apparatus is connected to the vascular system via a single access device and is configured to operate in a repeating sequence of a blood withdrawal period in which said at least one blood pumping device is operated to draw blood from the vascular system via the access device into a container, a blood return period in which said at least one blood pumping device is stopped and the blood flows from the container back into the vascular system via the access device, and wherein the monitoring method generates the time-sequence of parameter values during the blood return period, and evaluates the parameter values generated during the blood return period for detection of cardiac arrest.

47. The monitoring method of claim 29, further comprising a step of modifying the detection criterion as a function of one or more operating parameters of the extracorporeal blood processing apparatus.

48. The monitoring method of claim 29, wherein the first pressure sensor is arranged upstream of the blood processing unit and said at least one blood pumping device in an extracorporeal blood circuit in the extracorporeal blood processing apparatus, and wherein the pressure pulsations originating from heartbeats in the subject are superimposed on a baseline pressure level in the first pressure signal, wherein the alarm signal is generated only in absence of a recent change in the baseline pressure level.

49. A computer-readable medium comprising computer instructions which, when executed by a processor, cause the processor to perform the method of claim 29.

\* \* \* \* \*